(12) United States Patent
Moreau et al.

(10) Patent No.: US 10,512,399 B2
(45) Date of Patent: Dec. 24, 2019

(54) PHYSIOLOGICAL PARAMETER MONITORING DEVICE

(71) Applicant: OPHTIMALIA, Colombelles (FR)

(72) Inventors: Oliver Moreau, Cahagnes (FR); Franck Pasquette, Colombelles (FR); Xavier Razavet, Cairon (FR); Luc Mezenge, Rots (FR); Philippe Cauvet, Caen (FR); Peter Biermans, Bieville-Beuville (FR)

(73) Assignee: OPHTIMALIA, Colombelles (FR)

( * ) Notice: Subject to any disclaimer, the term of this patent is extended or adjusted under 35 U.S.C. 154(b) by 305 days.

(21) Appl. No.: 15/523,853

(22) PCT Filed: Nov. 2, 2015

(86) PCT No.: PCT/EP2015/075383
§ 371 (c)(1),
(2) Date: May 2, 2017

(87) PCT Pub. No.: WO2016/071253
PCT Pub. Date: May 12, 2016

(65) Prior Publication Data
US 2018/0303340 A1    Oct. 25, 2018

(30) Foreign Application Priority Data
Nov. 6, 2014 (EP) ..................... 14306783

(51) Int. Cl.
*A61B 3/16* (2006.01)
*G01L 9/12* (2006.01)
(Continued)

(52) U.S. Cl.
CPC .................. *A61B 3/16* (2013.01); *G01L 9/12* (2013.01); *G02C 7/04* (2013.01); *G02C 11/10* (2013.01);
(Continued)

(58) Field of Classification Search
None
See application file for complete search history.

(56) References Cited

U.S. PATENT DOCUMENTS

2002/0193674 A1    12/2002    Fleischman et al.
2013/0225968 A1    8/2013    Auvray et al.
2014/0296688 A1    10/2014    Lam et al.

FOREIGN PATENT DOCUMENTS

EP    0061777 A2    10/1982
FR    3001377 A1    8/2014
(Continued)

OTHER PUBLICATIONS

Extended European Search Report, dated Apr. 22, 2015 in European Patent Application No. 14306783.3.

*Primary Examiner* — Eric F Winakur
*Assistant Examiner* — Marjan Fardanesh
(74) *Attorney, Agent, or Firm* — Barnes & Thornburg LLP; Jeffrey Stone

(57) ABSTRACT

The invention relates to a physiological parameter monitoring device (100) comprising a first contact lens element (102) having an inner surface (103) and an outer surface (104) opposite the inner surface (103), a second contact lens element (110) having an inner surface (111) and an outer surface (112) opposite the inner surface (111), wherein the first contact lens element (102) and the second contact lens element (110) are attached to one another at a peripheral attachment area (109), thereby enclosing an intermediate space (105), and further comprising a passive sensing means (101) forming a resonant circuit for detecting variations of said physiological parameter, wherein the passive sensing means (101) is provided only in or on the first contact lens element (102).

20 Claims, 13 Drawing Sheets

Figure 1:
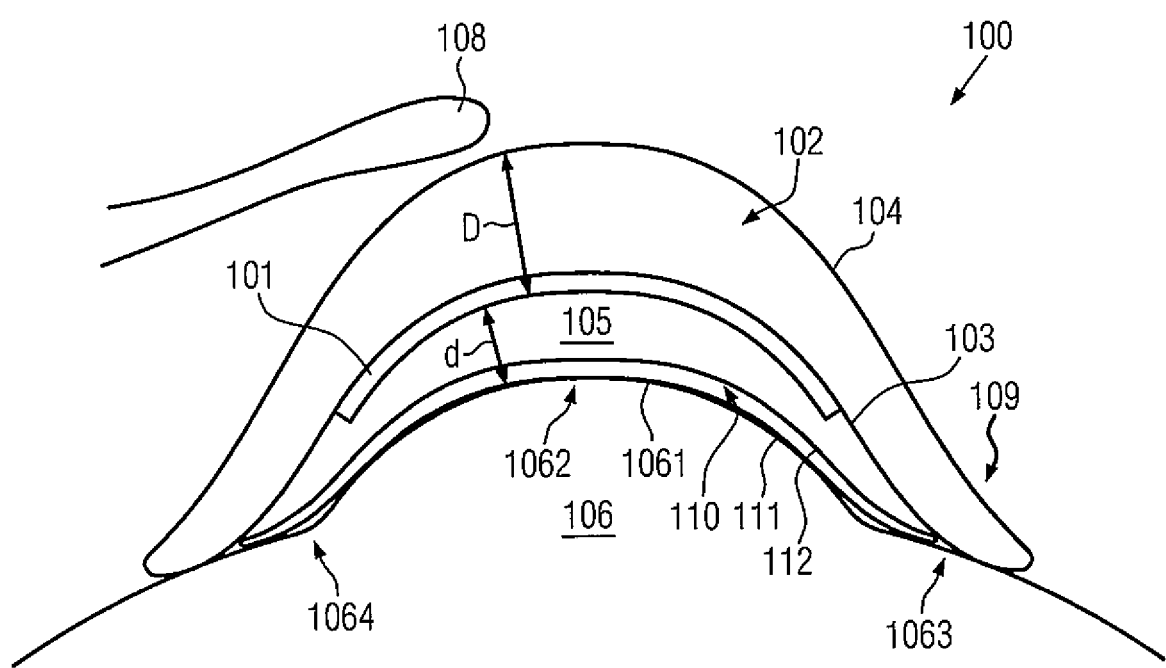

(51) Int. Cl.
*G02C 7/04* (2006.01)
*G02C 11/00* (2006.01)

(52) U.S. Cl.
CPC . *A61B 2562/0247* (2013.01); *A61B 2562/164* (2013.01)

(56) References Cited

FOREIGN PATENT DOCUMENTS

| | | |
|---|---|---|
| FR | 3001378 A1 | 8/2014 |
| RU | 2011121846 | 12/2012 |
| WO | 2009/111726 | 9/2009 |

PHYSIOLOGICAL PARAMETER MONITORING DEVICE

FIELD OF THE INVENTION

The present invention relates to the field of physiological parameter monitoring systems, in particular for monitoring variations of intraocular pressure. The invention relates in particular to a physiological parameter monitoring device, forming in particular a multilayered contact lens, with a passive sensing means for detecting variations of the physiological parameter.

BACKGROUND OF THE INVENTION

Intraocular pressure is one of the physiological parameters that allows diagnosis and monitoring of eye diseases such as glaucoma. Recently, portable and non-invasive sensing means and methods have been developed in order to measure daily variations of a patient's intraocular pressure, avoiding invasive surgical procedures where sensing means would need to be implanted in a patient's eye. Furthermore, the portability of non-invasive systems has the advantage that patients are no longer required to be immobilized at a hospital or clinic, but that the physiological parameters can now be continuously monitored in daily life situations.

Non-invasive sensing means known in the art usually comprise a sensing device that can be incorporated in a carrier device, such as a contact lens, which will be carried by a patient for monitoring purposes. Furthermore, the non-invasive sensing device can be used in combination with an external monitoring system that can receive and analyze data from the sensing means.

Different types of non-invasive sensing means for contact lenses are known, among which active sensors using miniaturized low power electronics such as microchips, active strain gages and the like, and therefore requiring an energy source. WO 2011/083105 A1 discloses for instance an active sensor comprising concentric strain gages and an associated microprocessor incorporated in a contact lens.

In contrast thereto, purely passive sensors have been developed in order to avoid using an energy source that might cause discomfort to a patient, for instance due to the generation of radiation in close vicinity of or even in direct contact with the patient's eye. A passive sensor is known from EP 2 412 305 A1, disclosing a portable physiological parameter monitoring system comprising a resonant LC circuit incorporated in a soft contact lens, wherein the resonant LC circuit responds to an external magnetic field generated by a complementary portable device, as known from instance from EP 2 439 580 A1, as well as a base station for analyzing the data acquired by the portable device. This type of passive sensor is known to rely on variations of the resonance frequency of the LC circuit incorporated in the contact lens as a function of variations of the intraocular pressure, as the latter should affect the shape of the surface of the eye and, consequently, also of the soft contact lens resting thereon. In turn, deformations of the soft contact lens should modify a capacitance of the resonant circuit.

However, the integration of sensors, passive or active, in soft contact lenses has been found to be more complex and more expensive than expected, preventing thus far a commercialization of portable intraocular pressure monitoring systems. A recurrent problem is that sensors are usually manufactured flat and subsequently bent to adopt the spherical cap shape of the over-molded lens, which has been found to create deformed areas in the final lens, for instance rippled edges, and sometimes also misalignments between the electrical components of the sensor. Thus, further to not being comfortable for wearing the lens, these deformations prevent a proper flat placement of the lens against the surface of the eye. As a consequence, the necessary sensitivity of the system to deformations of the surface of the eye cannot be reached.

It is also known from WO 2009/111726 A2 to provide surface deformation sensor comprising a contact lens formed by an external rigid layer and an internal soft layer bounded together at their edge, with a gap between the rigid and the soft layers, wherein a resonant LC circuit is split into components integrated in the rigid layer and components integrated in the soft layer, with electrical connection means therebetween. In particular, WO 2009/111726 A2 discloses a resonant LC circuit formed by an inductive coil and a sensing capacitor, wherein the inductive coil and an upper electrode of the capacitor are included in the rigid layer and electrically connected to a lower electrode included in the soft layer.

However, the fabrication of surface deformation sensor comprising such "multilayered hybrid" contact lenses requires various complex steps of integrating circuit components both in the rigid and in the soft layers, as well as the integration of a mechanism for electrically connecting the two layers. Furthermore, as they still include circuit components in the soft layer, such surface deformations sensors can also face the problems of unwanted ripples in the soft layer, and therefore the deformation of the soft layer may not reflect the actual deformation of the surface of the eye.

Thus, an objective of the present invention is to provide an improved physiological parameter monitoring device compared to intraocular pressure monitoring devices and surface deformation sensors known in the art. An objective of the present invention is also to provide an improved physiological parameter monitoring system using a multilayered contact lens and a passive sensor, which prevents or even avoids the aforementioned problems. Furthermore, common requirements of comfort of wearing and, as much as possible, unimpaired vision of the subject wearing the contact lens with integrated passive sensor should also be respected. Finally, an objective of the present invention is also to provide a physiological parameter monitoring device that improves the placement of the contact lens against the surface of an eye and the responsiveness of the passive sensor to surface deformations.

GENERAL DESCRIPTION OF THE INVENTION

The objective is solved with a physiological parameter monitoring device according to claim 1, in particular for detecting variations of intraocular pressure. The physiological parameter monitoring device comprises a first contact lens element with an inner surface and an outer surface opposite the inner surface, wherein at least the outer surface is adapted for contacting an ocular tissue, in particular eyelid tissue, and a second contact lens element with an inner surface and an outer surface opposite the inner surface, wherein at least the inner surface is adapted for contacting an ocular tissue, in particular at least the cornea and/or a tear film thereon. The first contact lens element and the second contact lens element are attached to one another at a peripheral attachment area, thereby enclosing an intermediate space. The physiological parameter monitoring device therefore can form a multilayered contact lens. The physiological parameter monitoring device further comprises a passive sensing means forming a resonant circuit for detecting variations of said physiological parameter, wherein said passive sensing means is provided only in or on the first contact lens element.

In contrast with systems known in the art using multilayered contact lenses, which do not address the existence of parasitic capacitances between conductive elements of the passive sensing means embedded in the contact lenses of physiological parameter monitoring systems and the nearby eye tissue, the physiological parameter monitoring system according to the present invention takes full advantage thereof. Since the physiological parameter monitoring system comprises a passive sensing means, which is a resonant circuit, parasitic capacitances affecting the resonance frequency can exist not only between the conductive, inductive and/or capacitive, elements of the passive sensing means as such, but also between these conductive elements and high relative permittivity layers in their vicinity, provided that there is an intermediate layer of low relative permittivity in-between. For instance, the intermediate space provided in a multilayered contact lens allows the existence of parasitic capacitances between conductive elements of the passive sensing means and the cornea and/or the tear film thereon, which can be predominant parameters in the resonance frequency. Thus, in a preferred embodiment, when the physiological parameter is the intraocular pressure, the first contact lens element can be rigid, and the second contact lens element can be soft. It is then possible to use a passive sensing means to build first electrodes of sensing capacitors, wherein the second electrodes thereof would be the underlying opposite surface of the eye and/or the tear film thereon. However, in variants, for other physiological parameters are measured, it would be possible to use two rigid lens elements, or two soft lens elements, or even a soft first lens element and a rigid second lens element.

In fact, in contrast to existing surface deformation sensors using multilayered contact lenses with passive sensors whose elements are integrated in both the rigid and the soft layer, the present invention takes advantage of the high relative permittivity of eye tissue and/or of the tear film thereon in order to avoid completely the integration of any circuit component of a passive sensor in the second contact lens element, as will become more obvious with the description of the embodiments. According to the invention, the tear film on the surface of the eye and/or the surface of the eye can be a "virtual" electrode forming a "parasitic" capacitance with the passive sensing means. Thus, in a preferred variant, when the second contact lens layer is a soft layer, no ripples can be formed and deformations of the soft layer correspond to deformations of the surface of the eye.

Advantageous optional features are described in the dependent claims and will also be described hereafter.

Preferably, said passive sensing means can be provided towards or over the inner surface of the first contact lens element. In preferred advantageous variants, the invention does no longer require the full incorporation of a passive sensor or of elements thereof in either of the first or second lens layers in order to be sensitive to eye surface deformations. Thus, a multilayered contact lens for the inventive device can be manufactured in simpler steps than in the prior art, as the passive sensing means could only be attached towards or over the inner surface of the first contact lens element, for instance using a layer of a biocompatible material.

Advantageously, the inner surface of said first contact lens element can comprise a recess for accommodating said passive sensing means. Thus, the attachment of a passive sensor to the inner surface of the first contact lens element is facilitated even more.

Advantageously, the intermediate space can be filled with a dielectric material. It is then also preferable that the dielectric material be compressible such that, when the second lens element is soft, deformations of the underlying surface can still be detected. In fact, following preferred variants, the intermediate space could be fully filled with a compressible dielectric material or partially filled with a mixture of compressible and incompressible dielectric materials, such that the deformations of the underlying surface can be detected. Although multilayered contact lenses known in the art usually enclose an intermediate space filled with air, it is always possible to fill said space with another dielectric material, preferably having also a low relative permittivity in order to allow the existence of parasitic capacitances between the passive sensor and the eye tissue and/or the tear film. In particular, the dielectric material can have a relative permittivity value, $\varepsilon_r$, of less than the relative permittivity of a tear film and/or an ocular tissue at ambient temperature, preferably less than about 10 times the relative permittivity of a tear film and/or ocular tissue at ambient temperature, more preferably a relative permittivity value, $\varepsilon_r$, between about 1 and about 5. Advantageously, decreasing the relative permittivity can increase the sensitivity. These ranges have proven to be advantageous for the detection of variations in the aforementioned parasitic capacitance.

Preferably, a distance between the passive sensing means and the inner surface of the second contact lens element can be smaller than a distance between the passive sensing means and the outer surface of the first contact lens element. The aforementioned parasitic capacitances could in principle also exist between the passive sensor and the eyelid and/or the tear film forming between the first contact lens element and the eyelid. Indeed, the relative permittivity of the eyelid and/or the tear film between the eyelid and the first lens element can be higher than that of the material used for the first lens element, which would then act as the intermediate dielectric in this parasitic capacitance. Thus, in order to avoid this unwanted parasitic capacitance, which could affect the resonance frequency, it is preferable that the distance from the conductive elements of the passive sensing means to at least the outer surface of the first lens element, that is the interface with the tear film forming thereon, is kept larger than the distance of the passive sensing means to the interface between the second lens element and the tear film on the cornea. In other words, it is also preferable that the first lens element is sufficiently thick to ensure that any unwanted parasitic capacitance with the eyelid and corresponding tear film is either completely avoided or becomes negligible compared to the parasitic capacitance between the passive sensing means and the cornea and associated tear film.

Preferably, the second contact lens element can be made of or comprise a flexible material, in particular a flexible polymer material, more in particular a hydrophilic flexible polymer material. Thus, the physiological parameter monitoring device can advantageously be used for detection surface deformations of the eye, in particular related to variations in the intraocular pressure, for instance when used for patients suffering from glaucoma.

Advantageously, in a variant of a preferred embodiment, the second contact lens element can be soft contact lens, in particular extending at least over the cornea. Thus, it is even possible to use directly a corrective or non-corrective soft contact lens and attach the same to the first contact lens element, which avoids further complex steps of manufacturing dedicated soft layers. An advantage thereof is that using directly existing soft contact lenses can avoid also completely the problem of ripple formation and flat placement against at least the cornea. Again, this variant is particularly adapted for monitoring deformations of the surface of the eye, and therefore also variations of the intraocular pressure.

In preferred variants of advantageous embodiments, the second contact lens element can extend over the cornea and part of the sclera leaving a non-contact area at the limbus. Most soft so-called corneal contact lenses are in fact also partially scleral and can therefore also be used in this variant. Leaving a non-contact area at the limbus of the eye can provide for a small depression allowing the second lens element, in this variant for instance a soft layer, in particular a soft contact lens, to stick flat against the surface of at least the cornea with help of the tear film.

Preferably, the first contact lens element can be made of or comprise a rigid material, in particular a rigid polymer material. This was found advantageous for attaching the passive sensing means to the first contact lens element, as it provides with a rigid attachment surface, thereby also avoiding any ripple formation in the first lens element compared to variants in which the first lens element would be a soft layer.

In a preferred variant, the first lens element can be a rigid contact lens, in particular a rigid scleral contact lens. Furthermore, in this variant, the peripheral attachment area can be an area for contacting the sclera. This variant was found advantageous in combination with a second contact lens element extending beyond the dimension of the cornea, in particular with a soft second lens element.

Advantageously, in preferred embodiments, the passive sensing means can be a resonant circuit comprising an inductor and at least one coplanar capacitor. Having coplanar capacitors allows a specific and advantageous geometry of the electric field lines generated in the resonant circuit, especially in comparison to passive sensors known in the art having sensing capacitive elements with a substantially face-to-face parallel electrode configuration or with their electrodes arranged on two different layers or planes of the contact lens. Coplanar capacitors can provide with a specific and advantageous electric field line geometry that allows taking advantage of the high relative permittivity of eye tissue and/or the tear film thereon for monitoring deformations of the surface of the eye.

Furthermore, said inductor can be a spiral inductor comprising a plurality of spires on a first main side of a carrier substrate, which can be coplanar with said at least one coplanar capacitor. An overall coplanar design for the conductive, inductive and/or capacitive, elements was found beneficial for taking advantage of possible parasitic capacitances with eye tissue and/or tear film, as a passive sensor can even be designed such that electric field lines will protrude out of the plane of the sensor, thereby facilitating the formation of parasitic capacitances with the surface of the eye and/or the tear film thereon, which can be used as sensing capacitors. In fact, the coplanar elements of the inventive passive sensing means, in other words the inductor and/or the at least one capacitor, form first electrodes of sensing capacitors using the parasitic capacitances existing with the underlying surface of the eye and/or tear film thereon when the passive sensing means is attached to a contact lens placed on the eye.

In variants of preferred embodiments, the inductor can further comprise at least one spire on a second main side of the carrier substrate, opposite the first main side. Depending on the allowed size for the passive sensing means and/or on the amplitude of the signal to be received by a complementary external antenna, configurations for which the inductor has at least one other spire on a second layer can be advantageous.

In such variants, the inductor can preferably comprise fewer spires on the second main side than on the first main side of the carrier substrate. While having similar amounts of spires was thought to be advantageous in passive sensors known in the art, with the inventive passive sensing means, it is more advantageous to have as many spires as possible only on the first main side, in other words on the side where they can be coplanar with said at least one capacitor. At least one spire, and sometimes a few more spires, are then provided on the second main side of the carrier substrate in order to increase the amplitude of the signal received by a complementary external antenna device which can be the device generating the external magnetic field while keeping the size, in particular the diameter, of the passive sensing means sufficiently small to be incorporated in a contact lens for use on a human eye.

Advantageously, said at least one spire on the second main side of the carrier substrate can be provided only at an outer circumference. In order to increase the signal amplitude, it is more advantageous to provide the at least one spire on the second main side only towards the outer circumference of the passive sensing means. Thus, several variants are possible, all compatible with each other. In one variant, in the thickness direction of the carrier substrate, the at least one spire of the second main side can be superimposed with at least one spire of the first main side. For instance, the outermost spires on either side of the carrier substrate can be superimposed. In another variant, it is also possible that the at least one spire of the second main side can be provided on a larger circumference than any of the spires of the first main side.

In some embodiments, the inductor can be ring-shaped and circular. This variant can be advantageous to increase the amplitude of the signal at the antenna of the complementary portable device generating the external magnetic field.

In other embodiments, the inductor can be a flat inductor comprising a plurality of, preferably three, concave arc-shaped segments with respect to a substantially central point of said passive sensing means, and wherein for at least one, preferably all, of the plurality of concave arc-shaped segments, the radius of curvature of said at least one segment at a point thereof is greater than the distance between said point and said substantially central point. Here, by the expression "arc-shaped", it should be understood that each arc-shaped inductor segment has, respectively, a curved geometry that follows essentially the shape of an arc of an ellipse, in particular an arc of a circle. Furthermore, while each arc-shaped segment can preferably be a continuous arc-shaped segment, a plurality of shorter back-to-back linear segments could also realize one longer segment having a globally arc-shaped geometry, which would also allow carrying out the invention. Also, by the expression "concave with respect to a substantially central point" and the like, it should be understood that the arc-shaped segments are all concave with respect to a same reference point of the passive sensing means, which can be about the geometrical center thereof, but which is not the center of any of the arc-shaped segments. Thus, the concave arc-shaped segments are not on a circle centered on this reference substantially central point.

Thus, in a preferred embodiment, the passive sensing means can have an inductive element with a structure comprising a plurality, preferably three, flap or ear-like segments that can be easily adapted to the concave cap shape of the first contact lens element because they allow controlling the areas of the passive sensing means that will be bent, folded and/or plastically deformed during the attachment to the inner surface of the first lens element. Given the typical dimensions of contact lenses and therefore the requirements on the dimension of passive sensing means, three concave arc-shaped inductor segments can provide a better compromise in terms of sensitivity and surface coverage, as well as in terms of flexibility for bending and attaching to the inner surface of the first lens element than more or less such segments. However, two, four or more concave arc-shaped segments with large radii should not be ruled out in variants of preferred embodiments. Furthermore, the curvature radii of the concave arc-shaped segments of the inductor can advantageously be chosen such that, once the passive sensing means is deformed for its attachment to the inner surface of the first lens element, they will essentially describe segments of a same predetermined circle of the inner surface of the first lens element.

In a variant of a preferred embodiment, the inductor can further comprise convex arc-shaped segments arranged between the concave arc-shaped segments. Here, the expression "convex arc-shaped segments" should be understood in a manner similar to "concave" as explained above. Thus, the convex arc-shaped segments are convex with respect to a substantially central point of the passive sensing means, as explained above. In this way, the areas where the passive sensing means can be bent during the attachment to the first contact lens element can be controlled.

In a further variant, the inductor can further comprises straight segments joining said convex arc-shaped segments to said concave arc-shaped segments, and the junctions between said straight segments and the concave arc-shaped segments can preferably be rounded. The length of the joining straight inductor segments can be used to better control the amount of material between the concave arc-shaped segments. Rounded junctions between successive inductor segments provide smoother shapes than rough pointy edges and are thus easier to attach to the concave cap shape of the first contact lens element. Here, attention should be brought to the fact that, while in this variant the rounded junctions could thus be concave-shaped, they are however not concave "with respect to the center point", unlike the "concave arc-shaped segments" as explained above.

Preferably, the inductor can comprise 5 to 20 spires, preferably 8 to 15 spires, more preferably 10 to 13 spires, on the first main side of the carrier substrate. When the inductor also comprises at least one spire on a second main side of the carrier substrate, it could have for instance up to 5 spires on said second main side. Also, in preferred embodiments of this variant, the width of the spires and/or the distance between spires can be in a range from about 30 μm to about 100 μm, preferably about 40 μm to about 80 μm. Thus, the invention allows combinations of number of spires and dimensions that can advantageously allow a subject wearing the inventive physiological parameter monitoring device to keep a clear vision. In particular, it is possible but not necessary that the width of the spires and the distance between successive spires are the same. Advantageously, the width of the inductor can be about 2 mm or less, preferably about 1.5 mm or less. The width of the inductor can in fact be greater than this value, but it is more advantageous that it is kept lower in order to keep the subject's vision clear.

Preferably, said at least one capacitor can comprise a first electrode and a second electrode, and said first and second electrodes can be coplanar with the spires of the inductor on the first main side of the carrier substrate, in particular only with the spires on the first main side when the inductor also has also at least one spire on the second main side. An advantage thereof is to facilitate the manufacturing process of the inventive passive sensing means by providing the electrodes of said at least one capacitor on the same main side of the carrier substrate. In addition, a passive sensing means, wherein the coplanar capacitor is coplanar with spires on one main side of the carrier substrate was found particularly advantageous for the structure of the electric field lines that allow taking advantage of parasitic capacitances forming with the surface of the eye and/or the tear film thereon.

In an advantageous variant of a preferred embodiment, said at least one capacitor can be provided at an inner circumference of the inductor, in particular of the spires on the first main side, more in particular towards a central area of the passive sensing means. Thus, while the inductor can provide for first electrodes of sensing capacitors on circumferential areas of the surface of the eye, the at least one physical capacitors can provide for first electrodes of sensing capacitors covering a surface within an inner circumference of the inductor, preferably over the cornea.

Furthermore, for at least one, preferably all, of the plurality of inductor concave arc-shaped segments, at least one capacitor can be provided at an inner circumference of said inductor concave arc-shaped segment towards a central area of said passive sensing means. This arrangement was found advantageous for bending the passive sensing means in view of its attachment to the inner surface of the first lens element. While it is possible that the passive sensing means works with only one capacitor, it is more advantageous in terms of sensitivity to include more than one capacitor. In a preferred variant, it is therefore possible to provide at least one capacitor at an inner side of each inductor concave arc-shaped segment. A configuration with two capacitors for each of the inductor concave arc-shaped segment was found even more advantageous in terms of sensitivity and surface coverage, while providing for sufficient visibility for a subject wearing the inventive physiological parameter monitoring device.

In a further variant, said at least one capacitor can be larger towards the inner circumference of the inductor than towards said central area. In preferred embodiments, a trapezoidal-like geometry of said at least one capacitor was found advantageous, as it can be easily bent to follow the concave cap geometry of the inner surface of the first contact lens element. The latter geometry was found advantageous in particular in combination with a circular ring-shaped inductor.

In another variant, said at least one capacitor can be partially arc-shaped following said inner circumference. Thus, the geometry of coplanar capacitors can advantageously be adapted to that of the inductor, in particular to that of the spires on the first main side, in order to increase the coverage of the surface of an eye, while still leaving at least a central zone free to allow for a sufficiently unimpaired vision. In particular, it is advantageous to adapt the geometry so that, once the passive sensing means is bent and attached to a contact lens, the initially coplanar elements cover as much of the underlying eye surface as possible while not impairing the vision.

Preferably, the first electrode of said at least one capacitor can be electrically connected to an inner circumference of the spires on the first main side of the carrier substrate, while the second electrode thereof can be electrically connected, in particular by means of an electrically conductive via, to an outer circumference of said inductor. When the inductor has at least one spire on a second main side of the carrier substrate, the connection can then be to said at least one spire on the second main side. While the actual sensing elements are provided in a coplanar manner, it is still possible to use electrically conductive vias for the electrical connections between the terminals of the circuit components. It is also possible to provide the first electrode of each capacitor as an extension of the spire on the inner circumference of the inductor. In other words, the first electrode of each capacitor can be integral with the spires of the inductor that are on the same main side of a carrier substrate.

Preferably, said at least one capacitor and/or the first electrode and the second electrode can be interdigitated. Following preferred variants, an interdigitated capacitor can have its electrodes interdigitated radially and/or circumferentially. In particular, the two electrodes of a coplanar capacitor could be interdigitated with one another radially and/or circumferentially, or each electrode could be interdigitated radially while being circumferentially coplanar with the other electrode. Interdigitated capacitors, which can also be coplanar, or more in general capacitors with interdigitated electrodes, were found advantageous to improve the sensitivity of the passive sensing means, while also providing an advantageous geometry of the electric field lines, which is favorable to the existence of the aforementioned parasitic capacitances.

Preferably, the passive sensing means can further comprise a central area free of inductor and/or capacitor material. Thus, a subject can keep a substantially clear vision while wearing a contact lens with the passive sensing means. The central area can be an area corresponding roughly to the average dimensions of the human pupil.

Preferably, the passive sensing means can further comprise a layer of a coating material over said inductor and said at least one capacitor and/or over the carrier substrate layer. The coating layer can be advantageous for protecting the circuit components, for instance from corrosion due to prolonged exposure to tears possibly filtering through the second contact lens element. Furthermore, the carrier substrate and/or the coating can preferably be removed following preferred contours of the passive sensing means. The problem of incorporating or attaching the passive sensing means to the inner surface of the first lens element is somewhat similar to wrapping a 3D surface with a 2D sheet. It is therefore advantageous to remove areas of carrier substrate that would create unnecessary material when deforming the passive sensing means to give it a curved shaped prior to the attachment. It is in fact preferable to remove as much carrier substrate as possible in order to make the passive sensing means as flexible as possible prior to its incorporation in a contact lens, while still leaving sufficient carrier substrate material in fragile areas, which could be subject to possible tears when the passive sensing means is bent.

Thus, compared to existing prior art intraocular pressure and/or surface deformation sensors, the inventive physiological parameter monitoring device can comprise a multilayered contact lens, which provides a mechanical means for producing detectable variations in the distance between the passive sensing means and a high relative permittivity layer corresponding to the surface of the eye or the tear film thereon, while the passive sensing means provides electrical means to measure said distance variation.

LIST OF FIGURES

Figure 2:
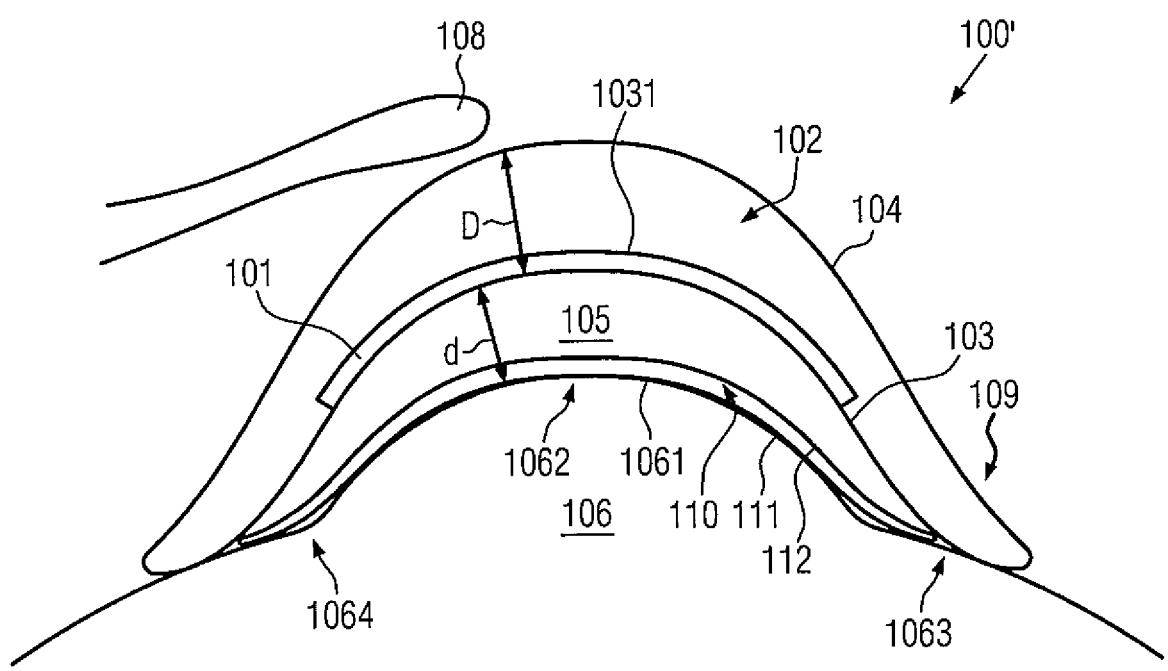
Figure 3:
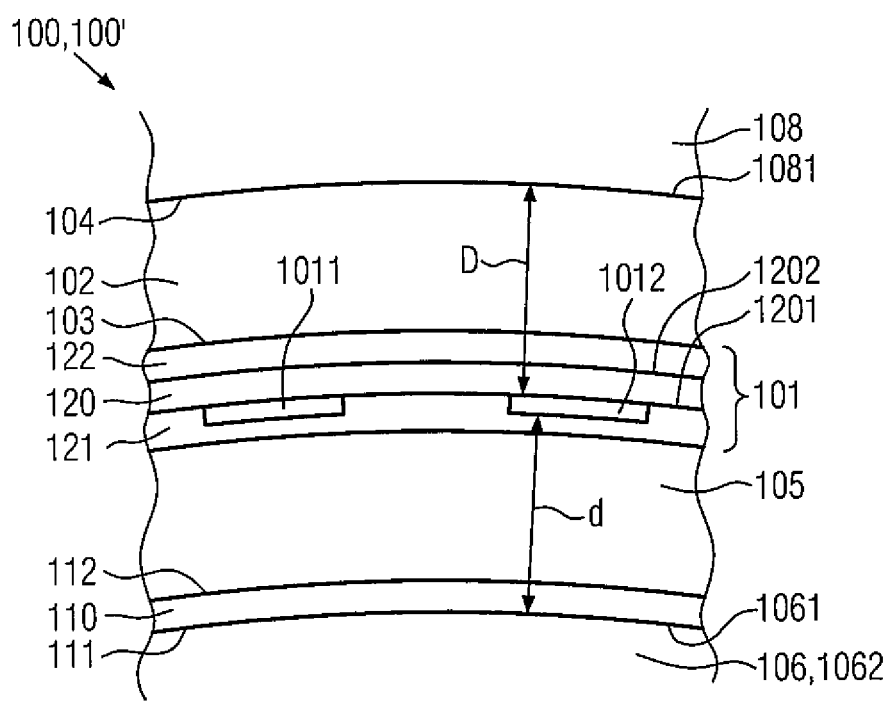
Figure 4:
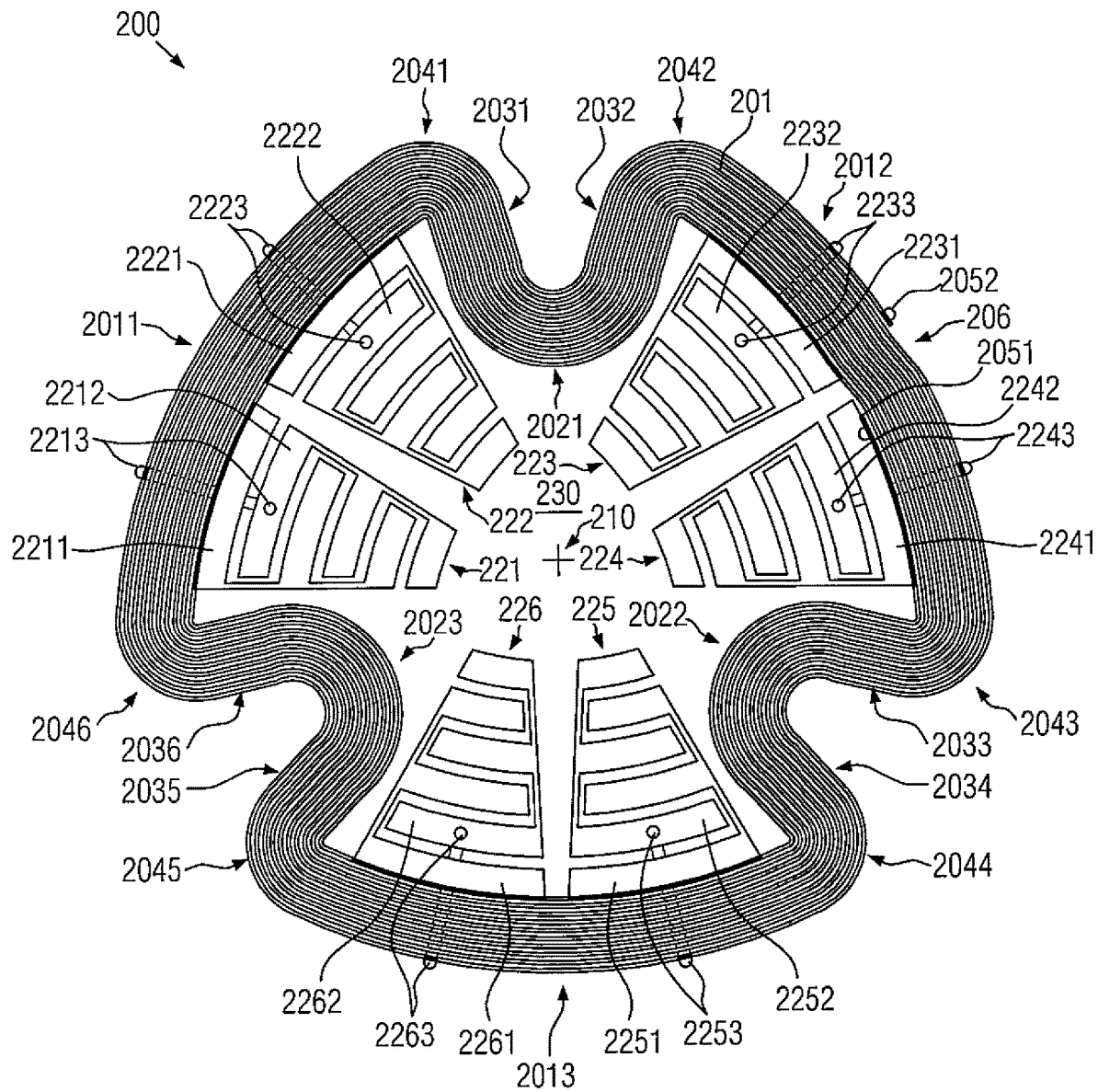
Figure 5:
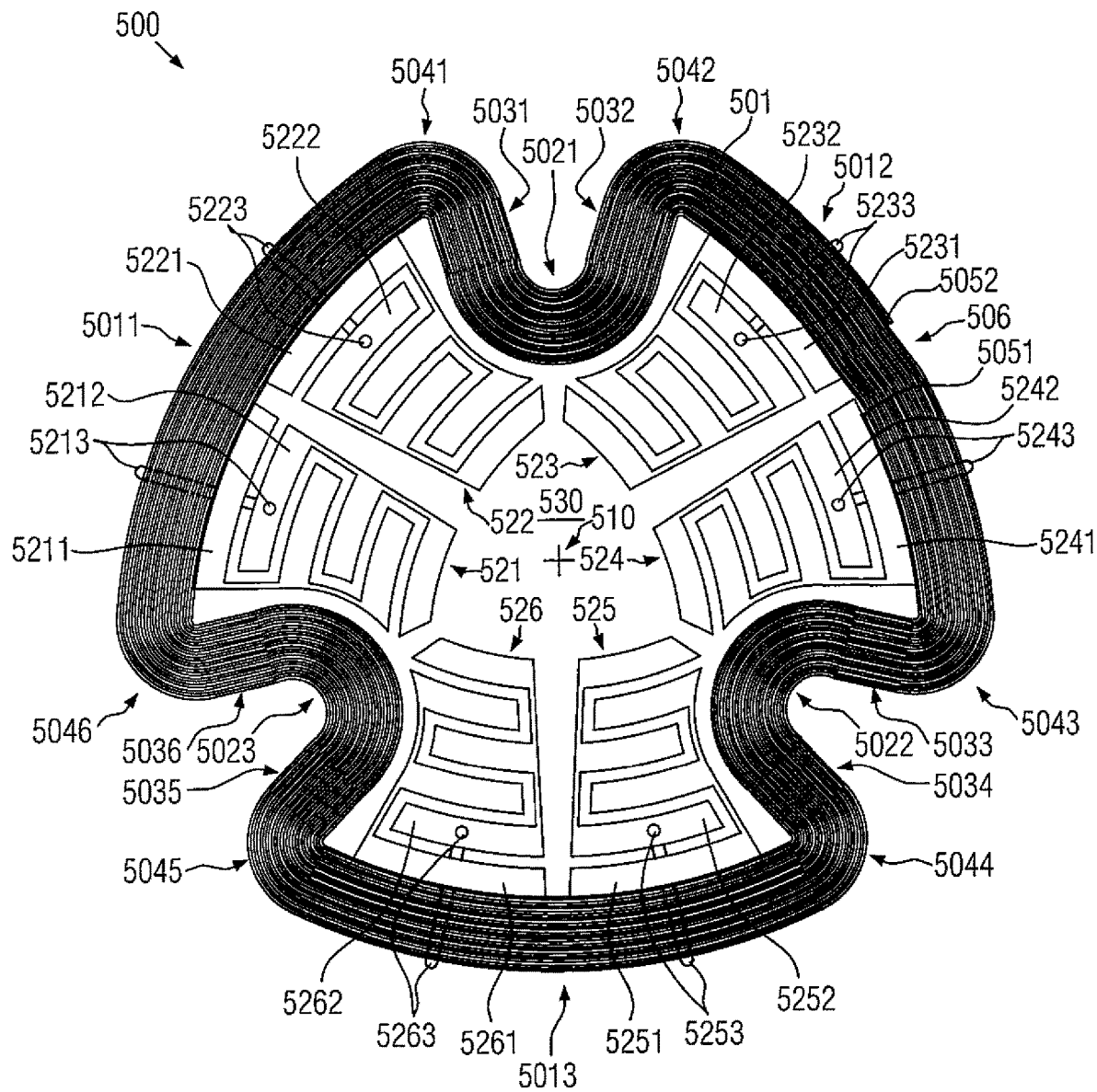
Figure 6:
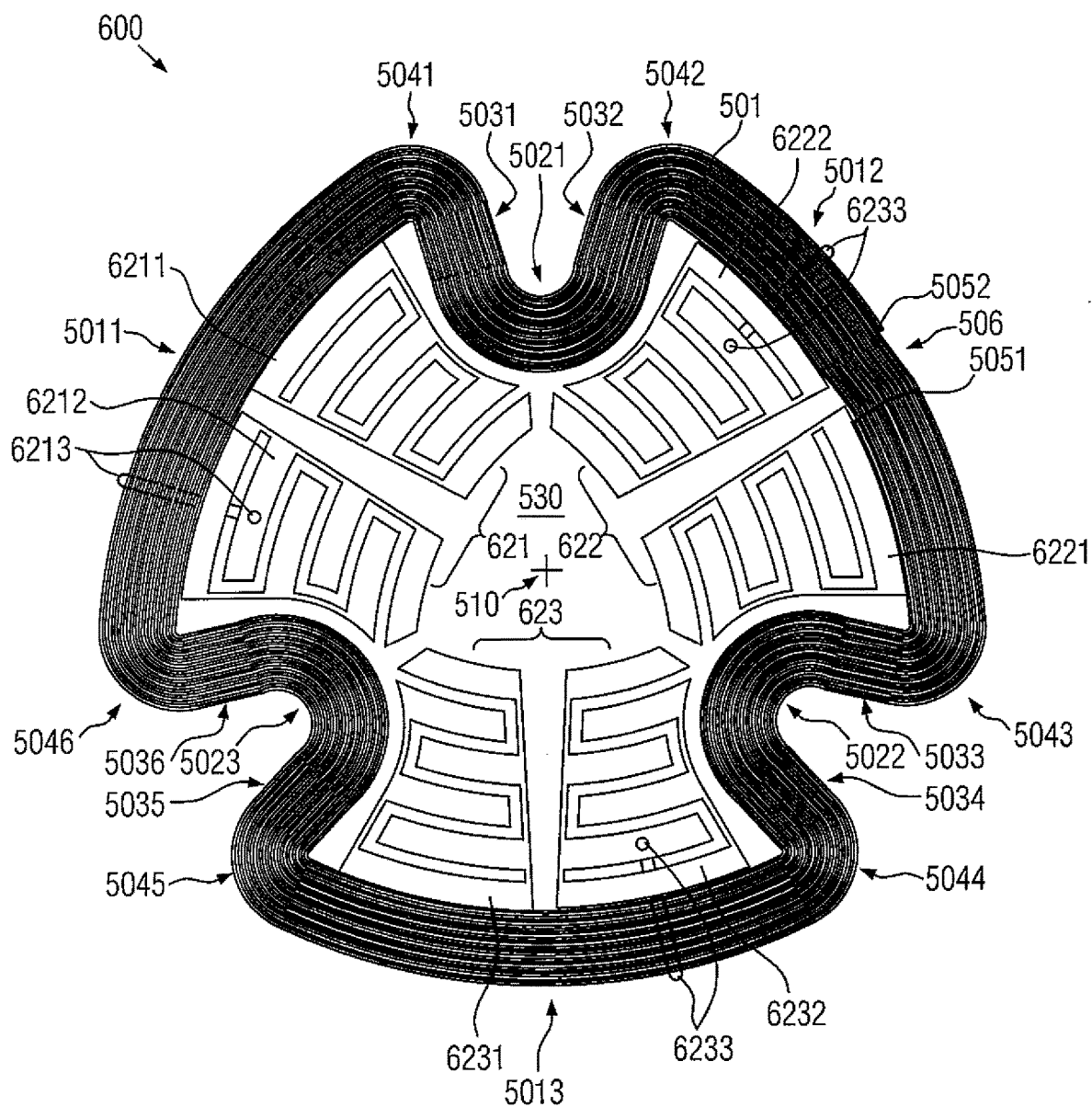
Figure 7:
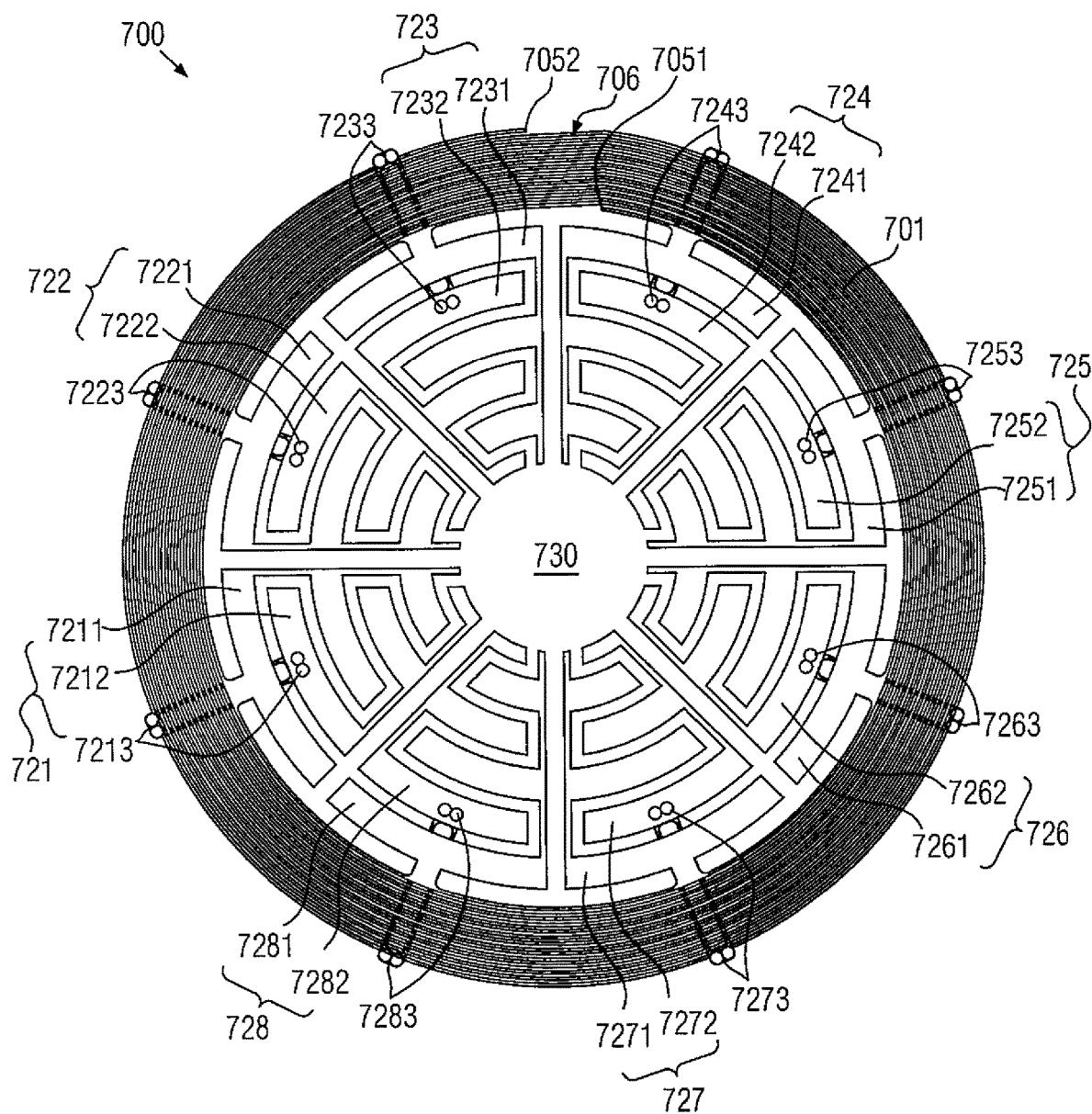
Figure 8:
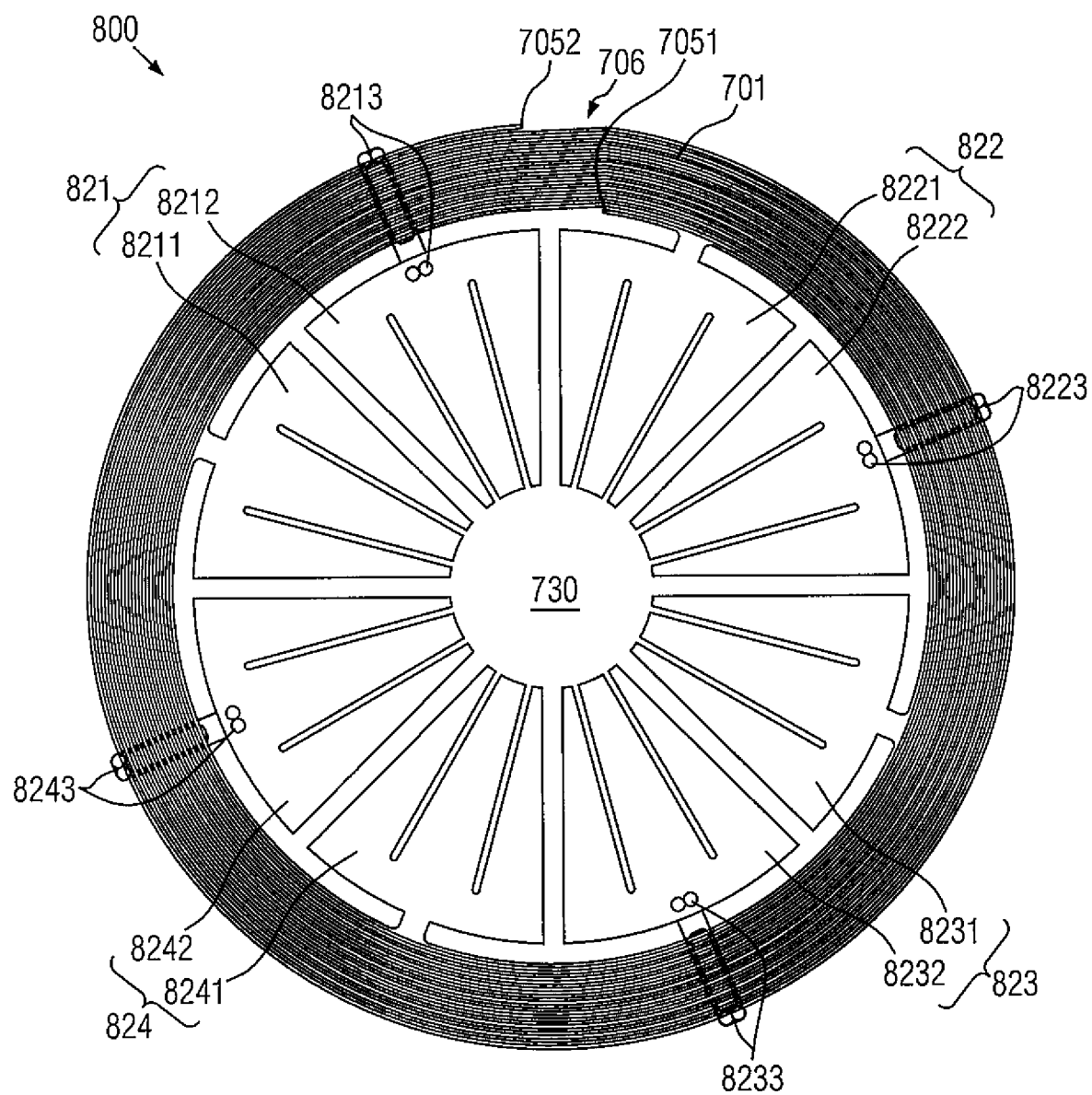
Figure 9:
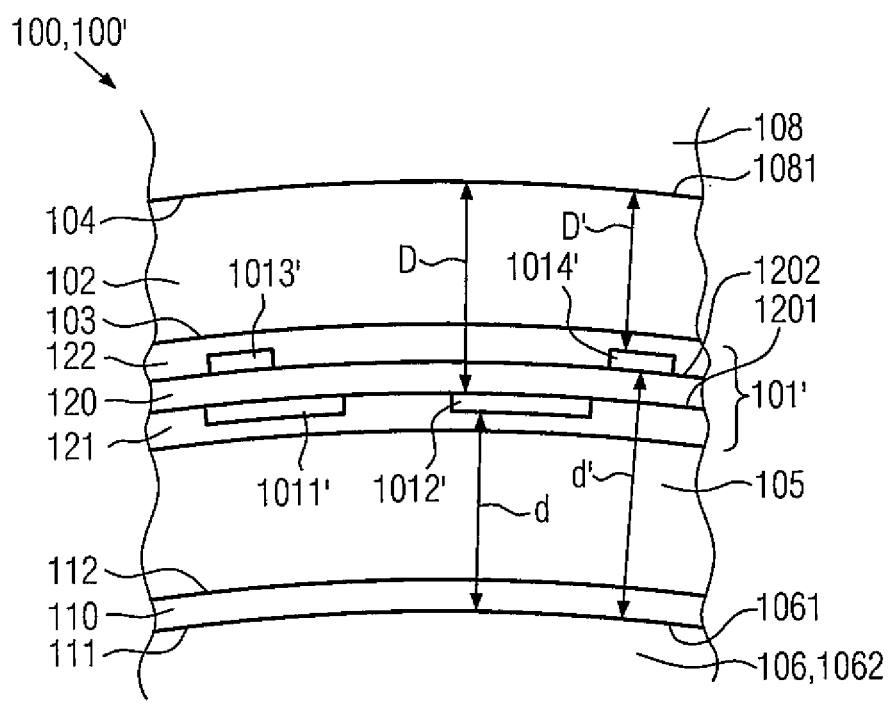
Figure 10:
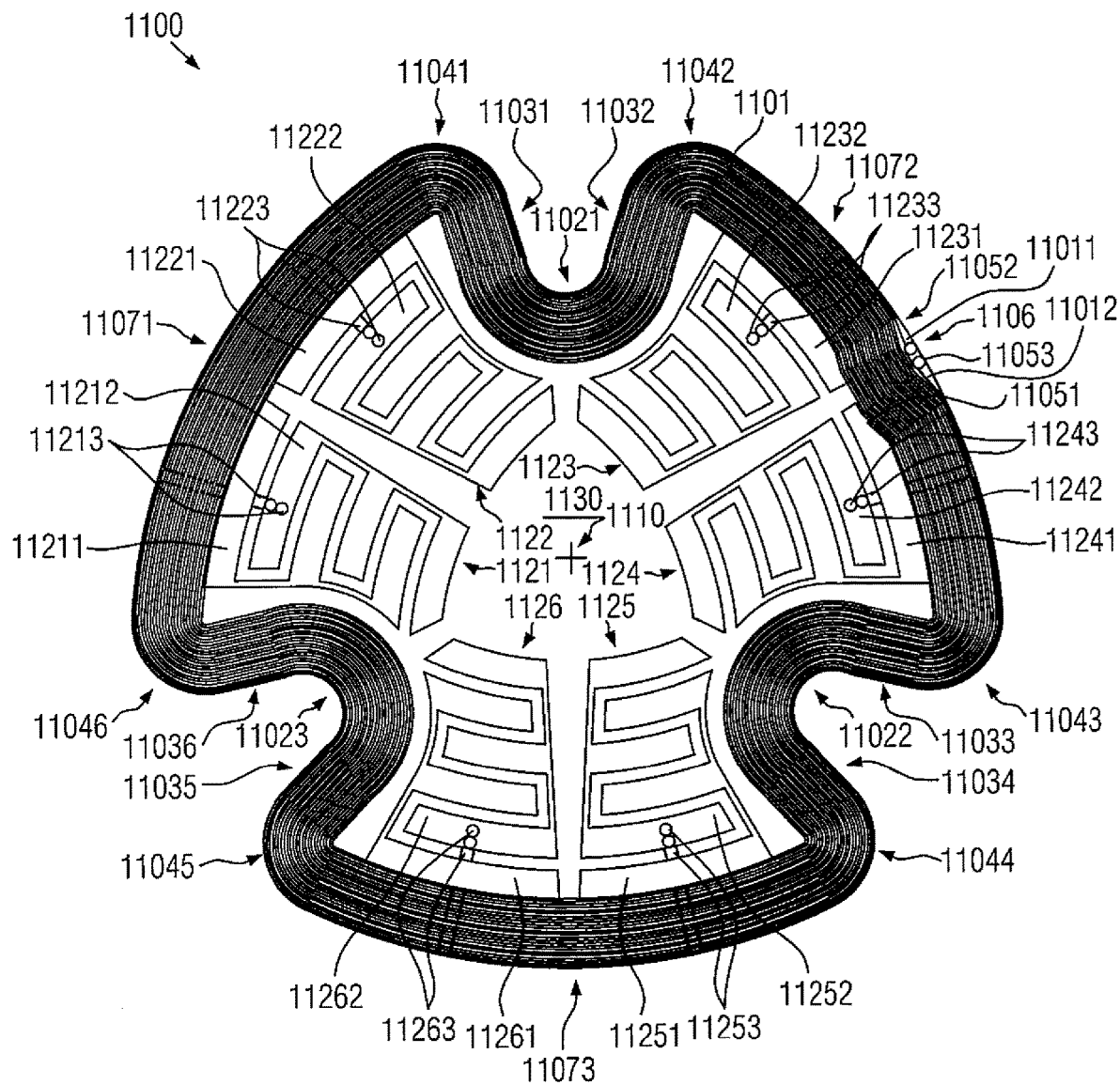
Figure 11:
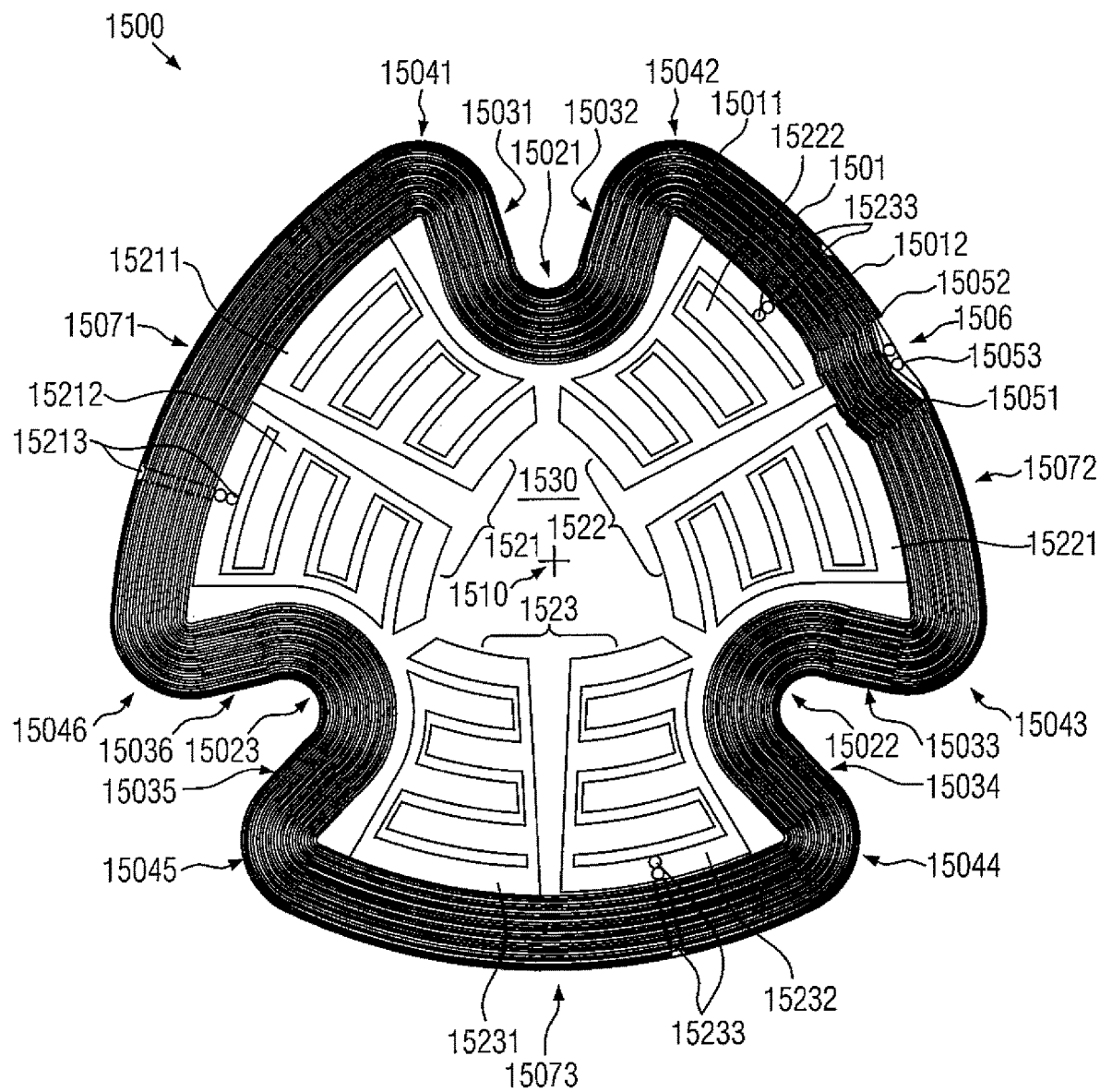

The invention will be described in more detail in the following, based on advantageous embodiments described in combination with the following figures:

FIG. 1 schematically illustrates an exemplary embodiment of a physiological parameter monitoring device;

FIG. 2 schematically illustrates a variant of the physiological parameter monitoring device illustrated in FIG. 1, in another exemplary embodiment;

FIG. 3 schematically illustrates a detail of the physiological parameter monitoring device illustrated in FIG. 1, in another exemplary embodiment, when used with one of the passive sensing means illustrated in FIGS. 4 to 8;

FIG. 4 schematically illustrates an exemplary passive sensor, which can be used in any of the embodiments of a physiological parameter monitoring device illustrated in FIGS. 1 to 3;

FIG. 5 schematically illustrates another exemplary passive sensor, which can also be used in any of the embodiments of a physiological parameter monitoring device illustrated in FIGS. 1 to 3;

FIG. 6 schematically illustrates another exemplary passive sensor, which can also be used in any of the embodiments of a physiological parameter monitoring device illustrated in FIGS. 1 to 3;

FIG. 7 schematically illustrates another exemplary passive sensor, which can also be used in any of the embodiments of a physiological parameter monitoring device illustrated in FIGS. 1 to 3;

FIG. 8 schematically illustrates another exemplary passive sensor, which can also be used in any of the embodiments of a physiological parameter monitoring device illustrated in FIGS. 1 to 3;

FIG. 9 schematically illustrates a detail of the physiological parameter monitoring device illustrated in FIG. 1, in another exemplary embodiment, when used with one of the passive sensing means illustrated in FIGS. 10 to 13;

FIG. 10 schematically illustrates an exemplary passive sensor, which can be used in any of the embodiments of a physiological parameter monitoring device illustrated in FIGS. 1, 2 and 9;

FIG. 11 schematically illustrates another exemplary passive sensor, which can also be used in any of the embodiments of a physiological parameter monitoring device illustrated in FIGS. 1, 2 and 9

Figure 12:
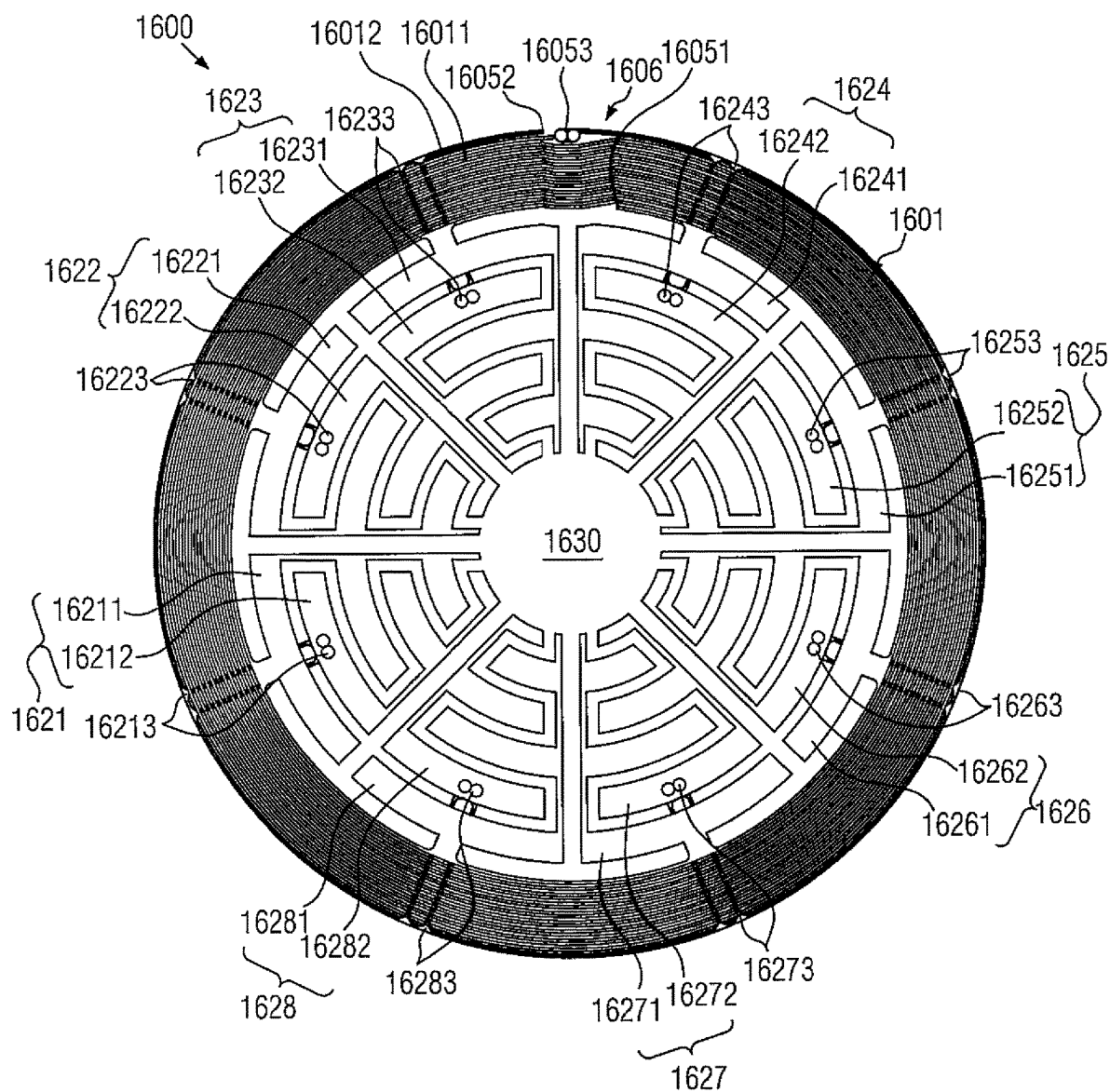
Figure 13:
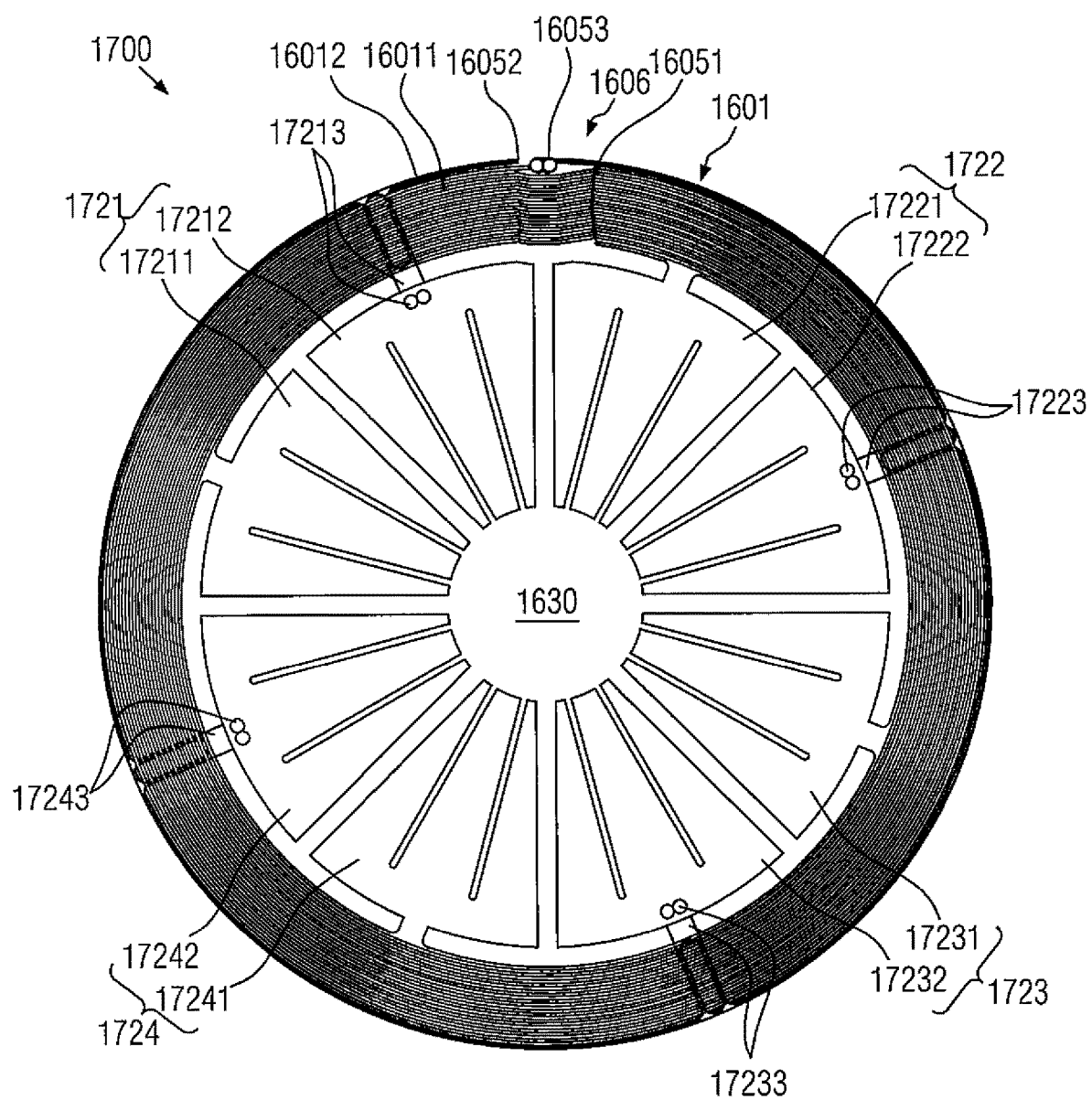

FIG. 12 schematically illustrates another exemplary passive sensor, which can also be used in any of the embodiments of a physiological parameter monitoring device illustrated in FIGS. 1, 2 and 9; and FIG. 13 schematically illustrates another exemplary passive sensor, which can also be used in any of the embodiments of a physiological parameter monitoring device illustrated in FIGS. 1, 2 and 9.

DESCRIPTION OF EMBODIMENTS

FIG. 1 illustrates an example of a physiological parameter monitoring device 100, which can be used for monitoring variations of the intraocular pressure, in particular by detecting deformations of the surface 1061 of an eye 106. The physiological parameter monitoring device 100 comprises a passive sensing means 101 forming a resonant circuit, which is attached at its backside to the inner surface 103 of a first contact lens element 102, such that the passive sensing means 101 can face the surface 1061 of the eye 106 on which the physiological parameter monitoring device 100 is resting. The arrangement is made preferably such that the passive sensing means 101 faces the area of the cornea 1062. For simplicity purposes, the passive sensing means 101 is illustrated as a single layer.

The layer comprising the passive sensing means 101 will be detailed in the embodiments illustrated in FIGS. 3 and 9. Examples of resonant passive sensors 200, 500, 600, 700, 800 and 1200, 1500, 1600, 1700 which could be used as the passive sensing means 101 in these embodiments will be detailed hereafter in further embodiments in reference to FIGS. 4 to 8 and 10 to 13. Also for illustrative purposes, FIG. 1 is represented as a cross-section view.

FIG. 2 illustrates a variant 100' of the physiological parameter monitoring device 100 illustrated in FIG. 1, which is essentially the same, with the exception that the passive sensing means 101 is accommodated in a recess 1031 provided in the inner surface 103 of the first contact lens element 102. This variant is then more advantageous than the variant illustrated in FIG. 1 in terms of stability. Otherwise, both variants are equivalent. Thus, in the following, reference will be made mostly to the variant illustrated in FIG. 1, but the skilled person will understand that further optional features and variants described in relation to FIG. 1 are also valid for the embodiment illustrated in FIG. 2.

FIG. 3 illustrates, in a cross-section, a detail of the physiological parameter monitoring devices 100, 100' illustrated in FIGS. 1 and 2, in a first variant, wherein the passive sensing means 101 could be any of the resonant passive sensors 200, 500, 600, 700, 800 of the embodiments illustrated in FIGS. 4 to 8. In turn, FIG. 9 illustrates a similar detail of the physiological parameter monitoring devices 100, 100', in a further variant, wherein the passive sensing means 101 could be any of the resonant passive sensors 1100, 1500, 1600, 1700 of the embodiments illustrated in FIGS. 10 to 13.

In the embodiment illustrated in FIG. 1, the first contact lens element 102 also comprises an outer surface 104 adapted for contacting eye tissue and/or a tear film thereon. A peripheral area 109 of the inner surface 103 of the first contact lens element 102 can be adapted for contacting at least the surface 1061 of the eye 106 and preferably also a tear film thereon, while the outer surface 104 can be adapted for contacting at least the eyelid 108 and preferably also a tear film. In this embodiment, the first contact lens element 102 is made of a rigid biocompatible material like used for rigid contact lenses, and it is preferably scleral, such that its peripheral area 109 rests on the surface 1061, in particular on the sclera 1063 of the eye 106 and/or on the tear film formed thereon (the tear film is not illustrated for simplicity), and such that an intermediate space 105, which can in particular be filled with air or with a biocompatible low relative permittivity material, as will be explained more in detail hereafter, is provided between the surface 1061 of the eye 106 and the passive sensing means 101.

In the exemplary embodiment illustrated in FIG. 1, the passive sensing means 101 is designed with a resonance frequency around 30 MHz, in particular with a frequency adapted for a medical use, such that the relative permittivity of a tear film is of the same magnitude as the relative permittivity of eye tissue, in particular the cornea, and much larger than the relative permittivity of air or of a biocompatible polymer lens material, such that $\varepsilon_r$ (cornea)$\approx\varepsilon_r$ (tear film)$>>\varepsilon_r$ (air)$\approx\varepsilon_r$ (lens material). Thus, in order to efficiently detect any deformation of the surface 1061 using a parasitic capacitance formed between the passive sensing means 101 and the surface 1061 of the eye 106, or in fact the tear film, it is necessary to avoid that the space 105 is filled with tear film.

Thus, as illustrated in FIG. 1, further to the first contact lens element 102, the physiological parameter monitoring device 100 also comprises a second contact lens element 110, preferably a layer of a flexible material, in particular a flexible polymer material, like for instance a soft contact lens, and both contact lens element 102, 110 are joined at the edge towards the peripheral area 109, enclosing the intermediate space 105. Thus, the physiological parameter monitoring device 100 forms a type of hybrid multilayered contact lens. The second contact lens element 110 also comprises an inner surface 111, adapted for contacting the surface 1061 of the eye 106, preferably also the tear film thereon, as well as an outer surface 112 opposite the inner surface 111.

Furthermore, in order to improve the contact between the soft contact lens element 110 and the surface 1061 of the eye 106, or in other words, in order to improve the responsiveness of the physiological parameter monitoring device 100 to deformations of the surface 1061, it is important that the soft contact lens element 110 can be positioned flat against the cornea 1062. Thus, following an advantageous variant, in the embodiment illustrated in FIG. 1, the physiological parameter monitoring device 100 is designed such that an area towards the peripheral area 109 avoids the limbus 1064 of the eye 106, while the peripheral area 109 itself rests on the sclera 1063, which creates a depression that helps maintaining the contact of the flexible lens element 110 on the eye 106.

Thus, in the embodiment illustrated in FIG. 1, the tear film on the surface 1061 of the eye 106 and the cornea 1062 can be considered essentially like one high relative permittivity layer, while the flexible lens layer 110 and the intermediate space 105 can be considered essentially like one single low relative permittivity layer, which allows the existence of a parasitic capacitance between the passive sensing means 110 and said high relative permittivity layer. In this embodiment, the intermediate space 105 can be filled with air, but in variants it could be filled with any other, preferably transparent, compressible and biocompatible dielectric material with a comparably low relative permittivity, which should be much lower than that of eye tissue and/or tear film near the resonance frequency, preferably at least about ten times lower, for instance $\varepsilon_r\approx 1$-5.

FIG. 3 schematically illustrates a detail, in a cross-section, of the physiological parameter monitoring device 100 or 100' illustrated in FIG. 1 or 2, respectively, focusing on the parasitic capacitances that can exist between the passive sensing means 101 and the surface 1061 of the eye 106, wherein the passive sensing means 101 can be a passive sensor 200, 500, 600, 700, 800 such as described in the embodiments referring to FIGS. 4 to 8. For the sake of simplicity, the tear film at the interface between the inner surface 111 of the second contact lens element 110 and the surface 1061 of the eye 106 can be considered to be one layer with the eye 106 and is therefore not illustrated.

In the exemplary embodiment illustrated in FIG. 3, the passive sensing means 101 is provided as a plurality of coplanar conductive elements 1011, 1012, which can be inductive and/or capacitive elements, forming a resonant circuit designed with a resonance frequency chosen in a range of frequencies preferably adapted for a medical use. For clarity purposes, only two such coplanar conductive elements 1011, 1012 are illustrated in the detailed view of FIG. 3. As mentioned previously, in a preferred variant of this embodiment, the passive sensing means 101 can be the passive sensor 200 of the embodiment illustrated with reference to FIG. 4 or any of the passive sensors 500, 600, 700, 800 of the embodiments illustrated in FIGS. 5 to 8. Thus, in a preferred variant, when the passive sensing means 101 is the passive sensor 200 of the embodiment illustrated in FIG. 4, two coplanar conductive elements 1011, 1012 can correspond to two successive coplanar conductive elements in a cross-section, for instance two successive spires of the spiral inductor 201 or two successive branches of either of the interdigitated capacitors 221, 222, 223, 224, 225, 226. However, variants of the passive sensor 200 such as the passive sensors 500, 600 illustrated in FIGS. 5 and 6 or other substantially coplanar passive sensors forming a resonant circuit, for instance the passive sensors 700, 800 of the embodiments illustrated in FIGS. 7 and 8, could be used instead.

In the variant illustrated in FIG. 3, the passive sensing means 101 of the exemplary embodiment illustrated in FIG. 1 can be provided on a layer 120 of a carrier substrate material, in particular on a front side 1201 thereof, with an optional layer 121 of a protective coating material being provided on or over the front side 1201 and/or the conductive elements 1011, 1012. Furthermore, the passive sensing means 101 can be attached to the first, rigid, contact lens element 102 of the physiological parameter monitoring device 100, 100' at the backside 1202 of the layer 120 of carrier substrate material. Thus, an optional layer 122 can also be provided over the backside 1202, of a coating material and/or an adhesive material.

As further illustrated in FIG. 3, the passive sensing means 101 attached to the first contact lens element 102 will be used to determine variations of a physiological parameter related to deformations of the surface 1061 of the eye 106. Thus, in the vicinity of the resonance frequency of the passive sensing means 101, the materials of the first contact lens element 102, and of the layers of substrate 120, coating 121, and coating and/or adhesive 122, are preferably chosen all very low in comparison to the relative permittivity of eye tissue, for instance of the cornea 1062, for instance preferably at least ten times lower.

The use of coplanar conductive, inductive and/or capacitive, elements 1011, 1012 provides with a different electric field lines geometry than capacitors with a face-to-face parallel electrode configuration, such that instead of having essentially straight electric field lines between two opposite parallel electrodes, the electric field lines in the coplanar configuration illustrated in FIG. 3 can also protrude out of the plane of the coplanar conductive elements 1011, 1012, for instance forming arcs. Parasitic capacitances can then exist between the conductive elements 1011, 1012, as well as between any conductive element 1012, 1012 and any other high relative permittivity elements in vicinity thereof if a dielectric material with a low permittivity is provided in-between, which can affect the resonance frequency of the passive sensing means 101.

In the variant illustrated in FIG. 3 of the embodiment illustrated in FIG. 1, the intermediate layer 105 and the second, flexible, contact lens element 110 are provided between the passive sensing means 101 and the layer 106 of high relative permittivity comprising the eye 106 and the tear film thereon. As mentioned above, the relative permittivity of said intermediate layer 105 and the relative permittivity of the material used for the second lens element 110 are low, preferably at least ten times lower, compared to the cornea 1062 and/or the corresponding tear film. Thus, since electric field lines can protrude out of the plane of the coplanar elements 1011, 1012, parasitic capacitances can also be formed between each of the coplanar conductive elements 1011, 1012 of the passive sensing means 101 and opposite areas of the surface 1061 of the eye 106, in particular of the cornea 1062, thereby forming a plurality of parasitic capacitances having substantially a parallel electrode configuration, wherein one electrode can be one of the conductive elements 1011, 1012 and the other electrode can be the opposite area of the surface 1061. In other words, the conductive elements 1011, 1012 of the passive sensing means 101 for instance the spires of the spiral inductor 201 and/or branches of the interdigitated capacitors 221, 222, 223, 224, 225, 226 in the embodiment illustrated in FIG. 4 form first electrodes of a plurality of sensing capacitors, and the areas opposite thereto on the surface 1061 form respective second electrodes of these sensing capacitors, without requiring physically built-in second sensing electrodes, in contrast with passive sensors known in the art. The deformation of the surface 1061 of the eye 106 will affect the distance between these "virtual" sensing electrodes, thereby also affecting the resonance frequency of the passive sensing means 101. This variation can, in turn, be detected using an external magnetic field following known methods.

Since the eyelid 108 is also a tissue with a high relative permittivity comparable to that of the cornea 1062, further parasitic capacitances could also exist between conductive elements 1011, 1012 of the passive sensing means 101 and opposite areas of the interface 1081 between the outer surface 104 of the first lens element 102 and the eyelid 108 and/or the tear film formed in-between, which could perturb the monitoring of the deformations of the surface 1061 of the eye 106. Thus, it is preferable that the physiological parameter monitoring device 100, 100', or multilayered contact lens, is manufactured in such a manner that, when the passive sensing means 101 is attached to the inner surface 103, a distance D from any of the coplanar conductive elements 1011, 1012 to the surface 1081 of the eyelid 108 or its tear film is greater than the distance d from said coplanar conductive element 1011, 1012 to the opposite area of the surface 1061 of the eye 106. In this way, the parasitic capacitances of the sensing capacitors can be main parameters varying as a function of the deformation of the surface 1061 of the eye 106, while any other capacitance of the physiological parameter monitoring device 100, 100' will either a fixed parameter or be negligible in comparison.

In a preferred variant of any of the embodiments illustrated with reference to FIGS. 1 to 3, the passive sensing means 101, which can be any of the passive sensors 200, 500, 600, 700, 800 of the embodiments illustrated in FIGS. 4 to 8, can be designed with an initial resonance frequency in the vicinity of 30 MHz. Near this frequency, the relative permittivity $\varepsilon_r$ for the different elements could then be: $\varepsilon_r$ (eyelid)≈80, and $\varepsilon_r$ (cornea)≈100 and $\varepsilon_r$ (tear film)≈80, such that it could be considered that $\varepsilon_r$ (cornea)≈$\varepsilon_r$ (tear film)≈$\varepsilon_r$ (eyelid) near 30 MHz. Furthermore, the relative permittivity of the materials forming the multilayered contact lens 102, 110 which could be rigid and/or flexible silicon or polymer materials, could be of the order of $\varepsilon_r$ (silicon)≈3, and that of the dielectric material in the intermediate space 105, which could be air or another low relative permittivity biocompatible dielectric material, could be $\varepsilon_r$ (dielectric)≈1-3. Thus, in the embodiments illustrated in FIGS. 1 to 3, the distance d from the passive sensing means 101 to the inner surface 111 of the soft lens 110, in other words to the interface between the soft contact lens element 110 and the tear film on the corneal area 1062, is smaller than the distance D between the passive sensing means 101 and the outer surface 104 of the rigid contact lens element 102, such that any parasitic capacitance between the passive sensing means 101 and the eyelid 108 will be either negligible or non-existent. For instance, without limiting the present invention to these values, the physiological parameter monitoring device 100, 100' could be designed such that d≈350 µm and D≈500 µm.

FIG. 4 illustrates a passive sensor 200 forming a resonant circuit for use in a contact lens, which can be used advantageously in the physiological parameter monitoring device 100, 100' of either of the embodiments illustrated in FIGS. 1 and 2, as explained in the variant illustrated in FIG. 3. Other flat passive sensing means could be attached to the inner surface 103 of the inventive physiological parameter monitoring device 100, but at least the passive sensor 200 was found advantageous in comparison to prior art multi-layered contact lenses with integrated passive sensors, as it also allowed to take advantage of the parasitic capacitances instead of having to integrate physical circuit elements in the flexible lens part. Variants of the passive sensor 200 that could be used following the embodiment explained with reference to FIG. 3 are described in further embodiments illustrated in FIGS. 5 to 8.

As can be seen in FIG. 4, the passive sensor 200 comprises an inductive element, here inductor 201, and at least one capacitive element, here the plurality of capacitors 221, 222, 223, 224, 225 and 226, which are all coplanar. In other words, prior to subsequent steps of attachment to the inner surface 103 of the first lens element 102, the passive sensor 200 is substantially flat such that it will form only one sensing layer also when it is deformed and attached to the inner surface 103. For instance, the passive sensor 200 can be provided on a layer of a carrier substrate, like in the embodiment illustrated in FIG. 3, with or without protective coating layers thereon, provided that the inductor 201 and the capacitors 221, 222, 223, 224, 225, 226 are provided in a coplanar manner.

Following a preferred variant, the inductor 201 of the embodiment illustrated in FIG. 4 is a flat inductive element, which can comprise a plurality of segments 2011, 2012, 2013 that are arc-shaped and concave with respect to a reference point, here the substantially central point 210 of the passive sensor 200, wherein this central point 210 does not need to be the geometric center of the sensor but can be close to it. As further illustrated in FIG. 4, these segments 2011, 2012, 2013 are in fact not centered on said substantially central point 210. Indeed, at least one segment 2011, 2012, 2013, and preferably all three segments 2011, 2012, 2013, has a curvature radius at a point thereof that is greater than the distance of said point to the substantially central point 210. Thus, following a preferred variant, the centers of the concave arc-shaped inductor segments 2011, 2012, 2013 can in fact be even outside the perimeter of the inductor 201. The inductor 201 then has the advantage that the flap-like or ear-like structure of the three segments 2011, 2012, 2013 will be easier to attach or to incorporate to the concave cap shape of a contact lens. In fact, it will be even possible to bend the sensor 200 such that the segments 2011, 2012, 2013 can substantially align on the same circle of the inner surface 103.

As also illustrated in FIG. 4, in order to further facilitate the attachment of the passive sensor 200 to the inner surface 103, for instance in the recess 1031 in the variant illustrated in FIG. 2, in particular to better control the areas that will bend during this process, the inductor 201 of the passive sensor 200 can further comprise inwards orientated, in other words convex with respect to the substantially central point 210, arc-shaped segments 2021, 2022, 2023 joining the concave segments 2011, 2012, 2013 to one another. Depending on the desired size of the passive sensor 200, FIG. 4 also illustrates that it is possible to join the concave segments 2011, 2012, 2013 to the convex segments 2021, 2022, 2023 via straight inductor segments 2031, 2032, 2033, 2034, 2035, 2036. Thus, the depth of the inwards pointing ear-like segments 2021, 2022, 2023 can be adjusted, thereby controlling the areas that will be bent during the attachment to the inner surface 103. FIG. 4 also illustrates an advantageous variant in which the junctions 2041, 2042, 2043, 2044, 2045, 2046 between the straight segments 2031, 2032, 2033, 2034, 2035, 2036 and the concave segments 2011, 2012, 2013 are rounded in order to provide a smoother shape.

Following yet another preferred variant, the inductor 201 can also be a flat spiral inductor. In the embodiment illustrated in FIG. 4, the inductor 201 spirals from a first terminal 2051 on its inner periphery, corresponding here to that of concave arc-shaped segment 2012, towards a second terminal 2052 on the outer periphery thereof. In order to obtain a segment 2012 essentially arc-shaped, the area 206 between the two terminals 2051, 2052 can present a small deflection, as illustrated in FIG. 4. The inductor 201 can further comprise a succession of spires, for instance about 5 to 20 spires, preferably 8 to 15 spires, more preferably 10 to 13 spires. In the embodiment illustrated in FIG. 4, the inductor 201 comprises for instance 10 spires.

Furthermore, following another preferred variant, since it is desirable that the total width of the inductor 201 in a radial direction, that is for instance with respect to central point 210, is kept below about 2.0 mm, for instance at about 1.5 mm or even below, in the embodiment illustrated in FIG. 4, the width of a spire can be about 60 µm, while the distance between successive spires could be about 75 µm. However, in other embodiments, the width of the spires and/or the distance between successive spires could be chosen in a range from about 30 µm to about 100 µm, preferably between about 40 µm and about 80 µm. In some embodiments, they could even be the same. For instance, it would be possible to have 15 spires with a width of about 50 µm and with a distance therebetween of also about 50 µm.

As further illustrated in FIG. 4, in contrast to capacitors with a face-to-face parallel electrode configuration, the capacitors 221, 222, 223, 224, 225, 226 are coplanar capacitors, meaning that their respective electrodes 2211 and 2212, 2221 and 2222, 2231 and 2232, 2241 and 2242, 2251 and 2252, and 2261 and 2262, are coplanar to one another, at least before bending or deforming the sensor 200 for its attachment to the first contact lens element 102. As explained above, the coplanar capacitors 221, 222, 223, 224, 225, 226 are therefore also coplanar with the spiral inductor 201. In particular, the electrodes 2211, 2212, 2221, 2222, 2231, 2232, 2241, 2242, 2251, 2252, 2261, 2262 are provided coplanar with the inductor 201, for instance on a same plane, in particular a same front side, of a carrier substrate (not illustrated for clarity purposes), as explained in reference to FIG. 3. Thus, electric field lines between two respective coplanar electrodes 2211 and 2212, 2221 and 2222, 2231 and 2232, 2241 and 2242, 2251 and 2252, 2261 and 2262 can also form arcs protruding out of the plane.

Furthermore, following an advantageous variant, the capacitors 221, 222, 223, 224, 225, 226 can also be interdigitated capacitors, as illustrated in FIG. 4. Thus, a given capacitor can comprise two essentially E-shaped electrodes facing each other such that their branches are interdigitated with one another. For instance, in FIG. 4, capacitor 221 comprises two essentially E-shaped coplanar and interdigitated electrodes 2211 and 2212. Similarly, the other capacitors 222, 223, 224, 225 and 226 are also provided in this manner.

Also following an advantageous variant, at least one capacitor is provided for each of the concave arc-shaped inductor segments 2011, 2012, 2013, at their inner periphery towards the central point 210. In the embodiment illustrated with reference to FIG. 4, following a preferred variant, two capacitors are provided for each concave arc-shaped inductor segments 2011, 2012, 2013. For instance, capacitors 221 and 222 are provided in segment 2011, while capacitors 223 and 224 are provided in segment 2012, and capacitors 225 and 226 are provided in segment 2013. Following a preferred variant, first electrodes of a given capacitor 221, 222, 223, 224, 225, 226, here electrodes 2211 and 2221, 2231 and 2241, and 2251 and 2261, can be electrically connected to an inner side—or inner circumference—of the inductor 201, here to the innermost spire of segments 2011, 2012 and 2013, respectively. In turn, second electrodes, here electrodes 2212 and 2222, 2232 and 2242, and 2252 and 2262, can be connected to an outer side—or outer circumference—of the inductor 201, here to the outermost spire of segments 2011, 2012 and 2013, respectively. While the first electrodes 2211, 2221, 2231, 2241, 2251, 2261 can be provided substantially as extensions of the innermost spire of inductor 201 towards the central point 210, the second electrodes 2212, 2222, 2232, 2242, 2252, 2262 can be connected to the outermost spire of the inductor 201 by means of respective electrically conductive vias 2213, 2223, 2233, 2243, 2253, 2263. For manufacturing reasons, these vias 2213, 2223, 2233, 2243, 2253, 2263 or electrical connections can be provided on a different plane, in particular a different side, of a substrate carrying the coplanar inductor 201 and capacitors 221, 222, 223, 224, 225, 226, provided that the passive sensor 200 is globally flat. As illustrated in FIG. 4, the electrically conductive vias 2213, 2223, 2233, 2243, 2253, 2263 can comprise, respectively, a conductive bridge and can cross the carrier substrate and, if necessary, also the second electrodes 2212, 2222, 2232, 2242, 2252, 2262.

In the embodiment illustrated with reference to FIG. 4, the capacitors 221, 222, 223, 224, 225, 226 can be larger towards the innermost spire of the inductor 201 than towards the central point 210, for instance such that the overall shape of each capacitor 221, 222, 223, 224, 225, 226 is essentially trapezoidal, with the larger base facing outwards from the central point 210 and the smaller base facing towards the central point 210. This shape can be advantageous for a subsequent bending of the passive sensor 200 in view of its attachment to the first contact lens element 102. This shape is, however, not limitative and other shapes could be used if they facilitate the attachment of the passive sensor 200 to a contact lens or the coverage of the surface 1061 of the eye 106, for instance like in the embodiments illustrated in FIGS. 5 and 6.

It is also preferable to remove unnecessary material from the passive sensor 200 in order to facilitate its attachment to the first contact lens element 102. Thus, it is advantageous to remove at least partially any unnecessary parts of the carrier substrate (not illustrated for clarity purposes), preferably following the inner and outer contours of the passive sensor 200, leaving however sufficient carrier substrate material in areas where bending the passive sensor 200 could damage the inductor 201 and/or any of the capacitors 221, 222, 223, 224, 225, 226. It is also preferably to leave a central area 230 surrounding the substantially central point 210, for instance corresponding to the position of the pupil, free of any material, such that the vision remains essentially unimpaired and the flexibility of the passive sensor 200 is improved.

FIGS. 5 to 8 illustrate further variants of passive sensors 500, 600, 700, 800 forming a resonant circuit for use in a contact lens, which can also be used advantageously in the physiological parameter monitoring device 100, 100' of either of the previous embodiments, following in particular the variant described with reference to FIG. 3. The reader is therefore referred back to the description above regarding any features of the passive sensors 500, 600, 700, 800 of the embodiments illustrated in FIGS. 5 to 8 that are analog to those of the passive sensor 200 illustrated in FIG. 4, as well as regarding their use in combination with any of the physiological parameter monitoring devices 100, 100' as described with reference to FIGS. 1 to 3.

In the embodiment illustrated in FIG. 5, like the passive sensor 200 of the embodiment illustrated in FIG. 4, the passive sensor 500 is a resonant circuit comprising an inductive element, here inductor 501, and at least one capacitive element, here the plurality of capacitors 521, 522, 523, 524, 525 and 526, which are all coplanar in one layer prior to any deformation of the passive sensor 500 for its incorporation in a contact lens of a physiological parameter monitoring device. The conductive, preferably metallic, elements 501, 521, 522, 523, 524, 525, 526 can also be provided on a layer of a carrier substrate, with or without protective coating layers thereon, which is again not illustrated for clarity purposes and can also be partially removed as described above.

Following a preferred variant, the inductor 501 of the embodiment illustrated in FIG. 5 is substantially of the same type and has the same properties and advantages as the inductor 201 of the embodiment illustrated in FIG. 4. In particular, it can also comprise concave arc-shaped segments 5011, 5012, 5013 with respect to—but not centered on—a substantially central reference point 510 of the passive sensor 500, as well as convex arc-shaped segments 5021, 5022, 5023 joining the concave segments 5011, 5012, 5013 to one another. Similarly, the inductor 501 can further comprise straight inductor segments 5031, 5032, 5033, 5034, 5035, 5036 and rounded junctions 5041, 5042, 5043, 5044, 5045, 5046 between the straight segments 5031, 5032, 5033, 5034, 5035, 5036 and the concave segments 5011, 5012, 5013.

Also like the inductor 201 illustrated in FIG. 4, the inductor 501 of the embodiment illustrated in FIG. 5 can also be a flat spiral inductor with a first terminal 5051 on the inner circumference of the concave arc-shaped segment 5012 and a second terminal 5052 on the outer circumference thereof, as well as a small deflected area 506. The inductor 501 can also comprise successive spires, for instance about 5 to 20 spires, preferably 8 to 15 spires, more preferably 10 to 13 spires, and its width can also preferably be kept below about 2.0 mm, for instance at about 1.5 mm or even below. In contrast with the inductor 201 of the embodiment illustrated in FIG. 4, the inductor 501 of the embodiment illustrated in FIG. 5 comprises 13 spires, which can have a width of about 50 μm and be spaced apart by also about 50 μm.

As further illustrated in FIG. 5, the capacitors 521, 522, 523, 524, 525, 526 can also be coplanar capacitors and are similar in almost all aspects to the capacitors 221, 222, 223, 224, 225, 226 of the embodiment illustrated in FIG. 4. For instance, the pairs of electrodes 5211 and 5212, 5221 and 5222, 5231 and 5232, 5241 and 5242, 5251 and 5252, and 5261 and 5262 can also be coplanar to one another and form interdigitated E-shapes. Here also, the capacitors 521, 522, 523, 524, 525, 526 are provided in a coplanar manner—prior to bending the sensor 500—with the inductor 501, with the corresponding advantages described above. Similarly, capacitors 521 and 522 are provided in segment 5011, while capacitors 523 and 524 are provided in segment 5012, and capacitors 525 and 526 are provided in segment 5013. Furthermore, the first electrodes 5211 and 5221, 5231 and 5241, and 5251 and 5261, can also be electrically connected to the innermost spire of the inductor 501 and be provided as extensions of or be integral with the innermost spire, while the second electrodes 5212 and 5222, 5232 and 5242, and 5252 and 5262, can be connected to the outermost spire by means of respective electrically conductive vias 5213, 5223, 5233, 5243, 5253, 5263, as described above.

In the embodiment illustrated in FIG. 5, and in contrast with the embodiment illustrated in FIG. 4, while the capacitors 521, 522, 523, 524, 525, 526 can also be larger towards the innermost spire of the inductor 501 than towards the central point 510, they broaden again towards the central area 530—which can be free of material—surrounding the central point 510, such that their extremities are partially arc-shaped, in particular following the geometry of the convex arc-shaped segments 5021, 5022, 5023, with the advantage over the embodiment of FIG. 4 that more underlying surface 1061 of the eye 106, in particular over the cornea 1062, can be covered once the passive sensor 500 is integrated in a physiological parameter monitoring device, for instance in any of the physiological parameter monitoring devices 100, 100'. In particular, as the innermost extremities of all electrodes 5211, 5212, 5221, 5222, 5231, 5232, 5241, 5242, 5251, 5252, 5261, 5262 become broader, the back of the E-shaped first electrodes 5211, 5221, 5231, 5241, 5251, 5261 follows partially the arc-shaped geometry of the nearby respective convex segment 5021, 5022, 5023.

In the embodiment illustrated in FIG. 6, the passive sensor 600 is also a resonant circuit comprising an inductive element, here the same inductor 501 as in the embodiment illustrated in FIG. 5, and at least one capacitive element, here the three capacitors 621, 622, 623, which are all coplanar in one layer prior to any deformation of the passive sensor 600 for its incorporation in a contact lens of a physiological parameter monitoring device. The reader is referred to the description above in particular regarding specifically the inductor 501, as well as other features in common with the passive sensors 200, 500 of the previous embodiments.

In contrast with FIGS. 4 and 5, only one capacitor 621, 622, 623 is provided at the inner circumference of each concave arc-shaped segment 5011, 5012, 5013, respectively. Like in the embodiments illustrated in FIGS. 4 and 5, each capacitor 621, 622, 623 of the embodiment illustrated in FIG. 6 is also coplanar, but the first and second electrodes in each pair of electrodes 6211 and 6212, 6221 and 6222, 6231 and 6232, are not interdigitated with each other. However, as illustrated in FIG. 6, each individual electrode 6211, 6212, 6221, 6222, 6231, 6232 is itself an interdigitated electrode. As further illustrated, each individual electrode 6211, 6212, 6221, 6222, 6231, 6232 of the passive sensor 600 can cover roughly at least as much surface as a full interdigitated capacitor 521, 522, 523, 524, 525, 526 of the passive sensor 500 of the embodiment illustrated in FIG. 5 or, in variants, as a full interdigitated capacitor 221, 222, 223, 224, 225, 226 of the passive sensor 200 of the embodiment referring to FIG. 4. In terms of shape, compared in particular to the embodiment illustrated in FIG. 5, in the embodiment illustrated in FIG. 6, each electrode 6211, 6212, 6221, 6222, 6231, 6232 roughly corresponds to having the two interdigitated E-shaped electrodes 5211 and 5212, 5221 and 5222, 5231 and 5232, 5241 and 5242, 5251 and 5252, and 5261 and 5262 of each capacitor 521, 522, 523, 524, 525, 526 joined at their largest extremity—towards the innermost spire of the inductor 501—thereby forming a single integral interdigitated electrode. An advantage of shaping the individual electrodes 6211, 6212, 6221, 6222, 6231, 6232 in this way is that it facilitates the molding or shaping of the passive sensor 600 for its attachment to a contact lens. As illustrated in FIG. 6, in an analog manner to the embodiment illustrated in FIG. 5, the back of the electrodes 6211, 6212, 6221, 6222, 6231, 6232 facing the convex arc-shaped segments 5021, 5022, 5023 of the inductor 501 can also follow the arc-shaped geometry of the convex arc-shaped segments 5021, 5022, 5023 and broaden towards the central area 530, with the same advantage over the embodiment of FIG. 4 that more underlying surface 1061 of the eye 106, in particular over the cornea, can be covered once the passive sensor 600 is integrated in a physiological parameter monitoring device, for instance in any of the physiological parameter monitoring devices 100, 100'.

Furthermore, like in the previous embodiments, the first electrodes 6211, 6221, 6231 of the passive sensor 600 can be electrically connected to the innermost spire of the inductor 501 and can be provided as integral extensions thereof, while the second electrodes 6212, 6222, 6232 can be connected to the outermost spire by means of respective electrically conductive vias 6213, 6223, 6233, which can also comprise a respective conductive bridge. FIG. 6 also illustrates that the vias 6213, 6223, 6233 can cross the carrier substrate and even the second electrodes 6212, 6222, 6232. An advantage of this configuration in the embodiment illustrated in FIG. 6 is, in comparison to the embodiments illustrated in FIGS. 4 and 5, that the number of electrically connecting vias is halved, thereby reducing the amount of areas where material crosses the carrier substrate, while keeping at least the same amount of surface covered by coplanar capacitors.

In the embodiment illustrated in FIG. 7, like the passive sensors 200, 500, 600 of the embodiments illustrated in FIGS. 4, 5 and 6, the passive sensor 700 is also a resonant circuit comprising an inductive element, here inductor 701, and at least one capacitive element, here the plurality of capacitors 721, 722, 723, 724, 725, 726, 727, 728 which are all coplanar in one layer prior to any deformation of the passive sensor 700 for its incorporation in a contact lens of a physiological parameter monitoring device. These conductive, preferably metallic, elements 701, 721, 722, 723, 724, 725, 726, 727, 728 can also be provided on a layer of a carrier substrate, with or without protective coating layers thereon, which is again not illustrated for clarity purposes and can also be partially removed as described above.

Following a preferred variant, in alternative to the embodiments illustrated in FIGS. 4, 5 and 6, the inductor 701 of the embodiment illustrated in FIG. 7 is a flat circular ring-shaped inductor spiraling from a first terminal 7051 on its innermost circumference towards a second terminal 7052 on its outermost circumference. While the inductors 201 and 501 of the previous embodiments and their variants can be more advantageous in terms of facilitating the deformation of the passive sensors 200, 500, 600 in view of their attachment to the concave cap-shape of a contact lens, the inductor 701 of the passive sensor 700 of the embodiment illustrated in FIG. 7 is in turn more advantageous in terms of the amplitude of the signal at the antenna of a complementary portable device generating the external magnetic field. Like in the previous embodiments, the inductor 701 can also comprise successive spires, for instance about 5 to 20 spires, preferably 8 to 15 spires, more preferably 10 to 13 spires, and its width can also preferably be kept below about 2.0 mm, for instance at about 1.5 mm or even below. Like the inductor 501 of the embodiment illustrated in FIGS. 5 and 6, the inductor 701 of the embodiment illustrated in FIG. 7 can thus comprises 13 spires, which can have a width of about 50 µm and be spaced apart by also about 50 µm.

In order to provide sufficient surface coverage in view of using the passive sensor 700 for detecting deformations of the surface of an eye while still providing for sufficient flexibility for an attachment to a contact lens, in the embodiment illustrated in FIG. 7, a plurality of capacitors are provided, here the eight coplanar interdigitated capacitors 721, 722, 723, 724, 725, 726, 727, 728. In view of the description above, the skilled person will understand that this number should not be seen as restrictive, and that more or less capacitors can be used depending on the desired configuration and sensitivity of the passive sensing means.

As further illustrated in FIG. 7, the capacitors 721, 722, 723, 724, 725, 726, 727, 728 are of the same type as the capacitors 221, 222, 223, 224, 225, 226 of the embodiment illustrated in FIG. 4. Thus, the pairs of electrodes 7211 and 7212, 7221 and 7222, 7231 and 7232, 7241 and 7242, 7251 and 7252, 7261 and 7262, 7271 and 7272, and 7281 and 7282 can also be coplanar to one another, forming interdigitated E-shapes. Furthermore, the capacitors 721, 722, 723, 724, 725, 726, 727, 728 can also be larger towards the innermost spire of the inductor 701 than towards the central area 730, for instance such that the overall shape of each capacitor 721, 722, 723, 724, 725, 726, 727, 728 is essentially trapezoidal, with the larger base facing outwards from the central area 730 and the smaller base facing towards said central area 730, with the same advantages as described above for instance for the embodiment illustrated in FIG. 4.

Furthermore, as described also for the embodiments illustrated in FIGS. 4 and 5, in the passive sensor 700 of the embodiment illustrated in FIG. 7, the first electrodes 7211, 7221, 7231, 7241, 7251, 7261, 7271, 7281 can also be electrically connected to the innermost spire of the inductor 701 and be provided as extensions of or be integral with the innermost spire, while the second electrodes 7212, 7222, 7232, 7242, 7252, 7262, 7272, 7282 can be connected to the outermost spire by means of respective electrically conductive vias 7213, 7223, 7233, 7243, 7253, 7263, 7273, 7283 as also described above for the previous embodiments.

In the embodiment illustrated in FIG. 8, the passive sensor 800 is also a resonant circuit comprising an inductive element, here the same inductor 701 as in the embodiment illustrated in FIG. 7, and at least one capacitive element, here the four capacitors 821, 822, 823, 824, which are all coplanar in one layer prior to any deformation of the passive sensor 800 for its incorporation in a contact lens of a physiological parameter monitoring device. The reader is referred to the description above in particular regarding specifically the inductor 701, as well as other features in common with the passive sensors 200, 500, 600, 700 of the previous embodiments.

In contrast with the embodiment illustrated in FIG. 7, but similarly to the embodiment illustrated in FIG. 6, in the passive sensor 800, the first and second electrodes in each pair of electrodes 8211 and 8212, 8221 and 8222, 8231 and 8232, 8241 and 8242 of the capacitors 821, 822, 823, 824 are not interdigitated with each other. However, as illustrated in FIG. 8, each individual electrode 8211, 8212, 8221, 8222, 8231, 8232, 8241, 8242 can be in the shape of a trident pointing towards the central area 730, forming also a trapezoidal shape as described above, wherein the capacitors 821, 822, 823, 824 are also larger towards the innermost spire of the inductor 701 than towards the central area 730, with again the same advantages as described above for instance for the embodiment illustrated in FIG. 4. As further illustrated in FIG. 8, each individual electrode 8211, 8212, 8221, 8222, 8231, 8232, 8241, 8242 of the passive sensor 800 can cover roughly at least as much surface as a full interdigitated capacitor 721, 722, 723, 724, 725, 726, 727, 728 of the embodiment illustrated in FIG. 7.

Furthermore, like in the previous embodiments, the first electrodes 8211, 8221, 8231, 8241 of the passive sensor 800 can be electrically connected to the innermost spire of the inductor 701 and can be provided as integral extensions thereof, while the second electrodes 8212, 8222, 8232, 8242 can be connected to the outermost spire by means of respective electrically conductive vias 8213, 8223, 8233, 8243 and respectively associated conductive bridges. Like in the embodiment illustrated in FIG. 6, an advantage of this configuration in the embodiment illustrated in FIG. 8 is, in comparison to the embodiment illustrated in FIG. 7, that the number of electrically connecting vias is halved, thereby reducing the amount of areas where material crosses the carrier substrate, while keeping at least the same amount of surface covered by coplanar capacitors.

As mentioned above, any of the passive sensors 200, 500, 600, 700, 800 of the embodiments illustrated in FIG. 4 to 8, or any variant thereof, can be used in the physiological parameter monitoring devices 100, 100' of the embodiments illustrated in FIG. 1 to 3 or variants thereof. Indeed, when the passive sensor 200, 500, 600, 700, 800 respond to an external magnetic field generated by a complementary portable device, the configuration of the inductor and/or of the capacitors in each of the passive sensors 200, 500, 600, 700, 800 allows the electric field lines generated therein to protrude out of the plane of the passive sensor 200, 500, 600, 700, 800. Thus, when used in any of the physiological parameter monitoring devices 100, 100', parasitic capacitances exist with the underlying eye tissue and/or tear film thereon, which will form sensing capacitors, wherein the spires of the inductor and/or the physical capacitors of the passive sensors 200, 500, 600, 700, 800 are first electrodes of said sensing capacitors, and the eye tissue and/or the tear film are the second electrodes thereof.

FIG. 9 schematically illustrates a detail, in a cross-section, of the physiological parameter monitoring device 100 or 100' illustrated in FIG. 1 or 2, respectively, focusing, like the variant illustrated in FIG. 3, on the parasitic capacitances that can exist between the passive sensing means 101, or here a variant 101' thereof, and the surface 1061 of the eye 106. In contrast with the passive sensing means 101 of the embodiment illustrated in FIG. 3, in the variant illustrated in FIG. 9, the passive sensing means 101' could be one of the passive sensors 1100, 1500, 1600, 1700 of the embodiments illustrated in FIGS. 10 to 13. Thus, the embodiments illustrated in FIGS. 3 and 9 are essentially the same and differ only in that variants of the passive sensing means 101, 101' are used in the physiological parameter monitoring systems 100, 100' of the embodiments illustrated in FIGS. 1 and 2. The description hereafter will therefore focus on the differences between the embodiments, and the reader is referred to the description above otherwise.

Like in the variant illustrated in FIG. 3, in the variant illustrated in FIG. 9, the passive sensing means 101' also comprises a plurality of coplanar conductive elements 1011', 1012' spread over the front side or first main side 1201 of the carrier substrate 120. For clarity purposes, again, only two coplanar such elements 1011', 1012' are illustrated in FIG. 9. However, in contrast, the passive sensor 101' can also comprise further conductive elements 1013', 1014' on the backside or second main side 1202 of the carrier substrate 120, opposite the first main side 1201. Following a preferred variant, the conductive elements 1013', 1014' on the backside 1202 can be provided only at the outermost circumference of the passive sensing means 101' and not towards the central area thereof, so that they overlap at most only with outermost conductive elements 1011', 1012' of the front side 1201.

In the variant illustrated in FIG. 9, although not represented for clarity purposes, the front side 1201 has many more conductive coplanar elements 1011', 1012' spread over its surface than the backside 1202 and, therefore, is the preferred side for facing the surface 1061 of the eye 106 to be monitored. In a preferred variant, when the passive sensing means 101' is the passive sensor 1100 of the embodiment illustrated in FIG. 10, or any of the passive sensors 1500, 1600, 1700 of the embodiments illustrated in FIGS. 11 to 13, the two coplanar conductive elements 1201', 1202' can correspond to two successive conductive elements on the first main side of the carrier substrate, in a cross-section, for instance two successive spires of the plurality of spires 11011 of the spiral inductor 1101 or two successive branches of either of the interdigitated capacitors 1121, 1122, 1123, 1124, 1125, 1126. Similarly, the elements 1203', 1204' can be schematic cross-sections of the spire 11012 on the second main side of the carrier substrate in the embodiment illustrated in FIG. 10. Furthermore, like in the previous embodiments and their variants, optional layers 121, 122 of protective coating and/or adhesive materials can also be provided on or over the front side 1201 and/or over the conductive elements 1011', 1012', as well as on or over the backside 1202 and/or, in this variant, over the conductive elements 1013', 1014', respectively.

Furthermore, like in the variant described with reference to FIG. 3, in the variant illustrated in FIG. 9, the passive sensing means 101' configured with coplanar conductive, inductive and/or capacitive, elements 1011', 1012' on the front side 1201 provides with an advantageous electric field lines configuration that results in parasitic capacitances existing between these conductive elements 1011', 1012' and the opposite surface 1061 of the eye 106 or of the tear film thereon, which are used as sensing capacitors to monitor the deformations in particular of the cornea 1062.

In the variant illustrated in FIG. 9, further "sensing" parasitic capacitances could exist between conductive elements on the backside 1202 of the carrier substrate 120 and the eye surface 1061, should these elements not be screened by a conductive element 1011', 1012' of the front side 1201, like for instance the conductive element 1014' in FIG. 9. This could be for instance the situation in the embodiments illustrated in FIGS. 10 to 13, wherein at least one spire 15012 or 16012 on the second main side of the carrier substrate has a larger diameter than any of the spires 15011 or 16012 on the first main side. In contrast, when conductive elements of the backside 1202 are screened by a conductive element of the front side 1201, as also illustrated in FIG. 2, wherein element 1013' is screened by element 1011', a constant parasitic capacitance can exist between these two elements 1011', 1013', which would only be a fixed parameter and therefore not build a sensing capacitor. This could be, in turn, the case in the embodiment illustrated with reference to FIG. 10, wherein the spire 11012 is screened by the outermost spire of the plurality of spires 11011.

Furthermore, like in the variant of FIG. 3, in the variant illustrated in FIG. 9 it is also preferable that the passive sensing means 101' is attached to the inner surface 103 of the first contact lens element 102 such that it is kept closer to the surface 1061 of the eye 106, in particular of the cornea 1062, than to the interface 1081 between the outer surface 104 of the first lens element 102 and the eyelid 108 and/or the tear film formed in-between. Thus, it is preferable that the first contact lens element 102 is manufactured in such a manner that the passive sensing means 101' can be attached thereto such that the distances D and D' from any of the coplanar conductive elements 1011', 1012' on the front side 1201 and from any of the coplanar conductive elements 1013', 1014' on the backside 1202 to the interface 1081 with the eyelid 108 are respectively greater than the distances d and d' from said coplanar conductive elements 1011', 1012' and 1013', 1014' to the opposite area of the surface 1061 of the eye 106. In this way, only the parasitic capacitances of the sensing capacitors can be main variable parameters as a function of the deformations of the eye surface 1061, while any other capacitance of the physiological parameter monitoring system 100, 100' will be either fixed or variable but negligible in comparison. Furthermore, it is also preferable that the thickness of the passive sensing means 101', in particular of the layer 120 of carrier substrate, or in other words the distance between the conductive elements 1011', 1012' of the front side 1201 and the conductive elements 1013', 1014' on the backside 1202, is sufficiently small to consider that D≈D' and d≈d', respectively.

Like for the embodiment referring to FIG. 3, in the embodiments illustrated in FIG. 1 or 2 in combination with the variant illustrated in FIG. 9, the passive sensing means 101', which can be any of the passive sensors 1100, 1500, 1600, 1700 of the embodiments detailed hereafter illustrated in FIGS. 10 to 13, can also be designed with an initial resonance frequency in the vicinity of 30 MHz. Near this frequency, the relative permittivity $\varepsilon_r$ for the different elements could then also be: $\varepsilon_r$ (eyelid)≈80, and $\varepsilon_r$ (cornea) ≈100 and $\varepsilon_r$ (tear film)≈80, such that it could also be considered that $\varepsilon_r$ (cornea)≈$\varepsilon_r$ (tear film)≈$\varepsilon_r$ (eyelid) near 30 MHz. Furthermore, the relative permittivity of the materials forming the multilayered contact lens 102, 110 which could be rigid and/or flexible silicon or polymer materials, could be of the order of $\varepsilon_r$ (silicon)≈3, and that of the dielectric material in the intermediate space 105, which could be air or another low relative permittivity biocompatible dielectric material, could be $\varepsilon_r$ (dielectric)≈1-3. The thickness of the carrier substrate layer 120, and therefore the distance between the spires 11011 on the first main side and the at least one spire 11012 on the second main side in the passive sensor 1100, or by analogy in any of the passive sensors 1500, 1600, 1700, can be less than about 100 μm, preferably even less than 50 μm. Thus, the distance d≈d' from the passive sensing means 101' to the inner surface 111 of the soft lens 110, in other words to the interface between the soft contact lens element 110 and the tear film on the corneal area 1062, is smaller than the distance D≈D' between the passive sensing means 101' and the outer surface 104 of the rigid contact lens element 102, such that any parasitic capacitance between the passive sensing means 101' and the eyelid 108 will be either variable but negligible or non-existent. For instance, without limiting the present invention to these values, the physiological parameter monitoring device 100, 100' could be designed such that d≈d'≈350 μm and D≈D'≈500 μm.

FIGS. 10 to 13 illustrate further passive sensors 1100, 1500, 1600, 1700 for a contact lens, which can also be used in the physiological parameter monitoring devices 100, 100' of the embodiments illustrated in FIGS. 1 and 2, in particular in combination with the variant described with reference to FIG. 9, in further exemplary embodiments. The reader is also referred back to the description above regarding the analogies between the embodiments.

Like in the embodiments illustrated in FIGS. 4 to 8, the passive sensor 1100 of the embodiment illustrated in FIG. 10 comprises an inductive element, here inductor 1101, and at least one capacitive element, here the plurality of capacitors 1121, 1122, 1123, 1124, 1125 and 1126, which are all provided as coplanar capacitors. Prior to subsequent steps of attachment to the first contact lens element 102 of the physiological parameter monitoring device 100, 100', the passive sensor 1100 is sufficiently thin to be considered substantially flat such that it forms essentially only one sensing layer, also when it is deformed, in particular bent, and attached to a contact lens of a physiological parameter monitoring system.

Furthermore, in contrast with the passive sensors 200, 500, 600, 700, 800, in the embodiment illustrated in FIG. 10, the inductor 1101 comprises a plurality of spires 11011 on a first main side of a carrier substrate and at least one other spire 11012 on a second main side of the carrier substrate, which is opposite the first main side. As explained above, the passive sensor 1100 can also optionally be provided with a coating layer, for instance on either main side of the carrier substrate or even on both sides thereof, in particular also over the inductor 1101 and/or the capacitors 1121, 1122, 1123, 1124, 1125, 1126. For the sake of simplicity, the carrier substrate and optional coating layer(s) are, however, not illustrated in FIG. 10. In the embodiment illustrated in FIG. 10, on the second main side of the carrier substrate, the inductor 1101 forms one spire 11012, which starts from a terminal 11052 on the outermost circumference, and which is then connected at its end to the beginning of the outermost spire among the spires 11011 of the first main side of the carrier substrate by means of one or more electrically conductive vias 11053 passing through the carrier substrate. The inductor 1101 then continues to spiral on the first main side of the carrier substrate, in the same spiral direction as on the second main side, with its outermost spire essentially overlapping the spire 11012 of the second main side, towards the central area 1130. The spires 11011 of the first main side then end with another terminal 11051 on their innermost circumference.

In fact, the spires 11011 on the first main side are essentially analog to the single sided spiral inductor 201, 501 of the embodiments illustrated in FIGS. 4 to 6. The area 1106 between the two terminals 11051, 11052 can thus present small deflections between successive spires, as illustrated in FIG. 10, in particular between successive spires 11011 on the first main side.

In the embodiment illustrated in FIG. 10, only one spire 11012 is provided on the second main side of the carrier substrate. However, in other embodiments, at least one outermost spire 11012 on the second main side of the carrier substrate could be provided on a larger circumference than that of any of the spires 11011 on the first main side. In such variants, it would then be also possible to have more than one spire 11012 on the second main side, for instance up to five, as long as there are more spires 11011 on the first main side than spires 11012 on the second main side. On the first main side, the inductor 1101 can comprise for instance about 5 to 20 spires 11011, preferably 8 to 15 spires 11011, more preferably 10 to 13 spires 11011. Thus, in the embodiment illustrated in FIG. 10, the inductor 1101 comprises for instance 12 spires 11011 on the first main side, and only one spire 11012 on the second main side.

As further illustrated in FIG. 10, similarly to the embodiments illustrated in FIGS. 4 to 6, in this embodiment, the inductor 1101 can also comprise a plurality of arc-shaped segments 11071, 11072, 11073 that are concave with respect to a substantially central point 1110 of the passive sensor 1100. Thus, the inductor 1101 can also further comprise inwards orientated, in other words convex with respect to the substantially central point 1110, arc-shaped segments 11021, 11022, 11023, as well as straight inductor segments 11031, 11032, 11033, 11034, 11035, 11036 joining the concave segments 11071, 11072, 11073 to one another, wherein the junctions 11041, 11042, 11043, 11044, 11045, 11046 therebetween can also be rounded. Thus, the overall geometry of the inductor 1101 can have the same advantages than that of the inductors 201, 501 of the previous embodiments.

Furthermore, following another preferred variant, since it is also desirable that the total width of the inductor 1101 in a radial direction, that is for instance with respect to central point 1110, is kept below about 2.0 mm, for instance at about 1.5 mm or even below, in the embodiment illustrated in FIG. 10, the width of a spire 11011, 11012 can be about 50 μm, while the distance between successive spires 11011 on the first main side can also be about 50 μm. However, in other embodiments, the width of the spires 11011, 11012 and/or the distance between successive spires 11011 or 11012 could be chosen in a range from about 30 μm to about 100 μm, preferably between about 40 μm and about 80 μm and don't need to be the same. Even if it is preferable that the spires 11011, 11012 on the first and second main sides of the carrier substrate have similar dimensions, in some embodiments the width and distance between spires 11011, 11012 on the first and second main sides could be different.

As further illustrated in FIG. 10, the capacitors 1121, 1122, 1123, 1124, 1125, 1126 are coplanar capacitors and can be for instance like the capacitors 221, 222, 223, 224, 225, 226 or 521, 522, 523, 524, 525, 526 of the passive sensors 200 or 500 of the embodiments illustrated in FIG. 4 or 5, respectively. Thus, their respective electrodes 11211 and 11212, 11221 and 11222, 11231 and 11232, 11241 and 11242, 11251 and 11252, and 11261 and 11262, are also coplanar to one another, at least before bending or deforming the sensor 1100 for its attachment to the first contact lens element 102. Thus, the coplanar capacitors 1121, 1122, 1123, 1124, 1125, 1126 are also coplanar with the spiral inductor 1101 on a main side of the carrier substrate, in particular with the spires 11011 of the inductor 1101 on the front side of the carrier substrate (not illustrated for clarity purposes). Thus, the configuration of the passive sensor 1100 also generates electric field lines between two respective coplanar electrodes 11211 and 11212, 11221 and 11222, 11231 and 11232, 11241 and 11242, 11251 and 11252, 11261 and 11262, or between the coplanar spires 11011 on the front side, that form arcs protruding out of the plane, which are necessary to have parasitic capacitances with the opposite surface 1061 of the eye 106.

Furthermore, as also illustrated in FIG. 10, and in particular like in the variant illustrated in FIG. 5, the capacitors 1121, 1122, 1123, 1124, 1125, 1126 can also comprise two essentially E-shaped electrodes facing each other such that their branches are interdigitated with one another, and they can be larger towards the innermost spire of the inductor 1101 than towards the central point 1110, with the larger base facing outwards from the central point 1110 and the smaller base facing towards the central point 1110 or the central area 1130. Furthermore, at least one capacitor can also be provided for each of the concave arc-shaped inductor segments 11071, 11072, 11073, at their inner periphery towards the central point 1110. The capacitors 1121, 1122, 1123, 1124, 1125, 1126 can also be arched so as to broaden again towards the central area 1130 and can be partially arc-shaped following the geometry of the convex arc-shaped segments 11021, 11022, 11023, with the advantages described above.

Furthermore, as illustrated in FIG. 10, following a preferred variant, first electrodes of a given capacitor 1121, 1122, 1123, 1124, 1125, 1126, here electrodes 11211 and 11221, 11231 and 11241, and 11251 and 11261, can be electrically connected to an inner side—or inner circumference—of the innermost spire of the spires 11011 of the inductor 1101, here to the innermost spire of segments 11071, 11072 and 11073, respectively, on the first main side of the carrier substrate, which is also the spire comprising the terminal 11051. In turn, second electrodes, here electrodes 11212 and 11222, 11232 and 11242, and 11252 and 11262, can be connected to an outer side—or outer circumference—of the inductor 1101, here to the outermost spire 11012 of segments 11071, 11072 and 11073, respectively, on the second main side of the carrier substrate, which comprises the other terminal 11052 of the inductor 1101. While the first electrodes 11211, 11221, 11231, 11241, 11251, 11261 can be provided substantially as integral extensions of the innermost spire of the plurality of spires 11011 on the first main side of inductor 1101 towards the central point 1110, the second electrodes 11212, 11222, 11232, 11242, 11252, 11262 can be connected to the spire 11012 of the inductor 1101 on the second main side by means of respective electrically conductive vias 11213, 11223, 11233, 11243, 11253, 11263 passing through the carrier substrate, and if necessary also through the second electrodes 11212, 11222, 11232, 11242, 11252, 11262 themselves, as illustrated in FIG. 10. As also illustrated in FIG. 10, the vias 11213, 11223, 11233, 11243, 11253, 11263 can comprise, respectively, a conductive bridge integral with the spire 11012.

As also mentioned in the previous embodiments, it is also preferable to remove unnecessary material, in particular carrier substrate material (not illustrated in FIG. 10 for the sake of simplicity), from the passive sensor 1100 in order to facilitate its attachment to the first contact lens element 102 of the physiological parameter monitoring system 100, 100'. It is also preferable to leave the central area 1130 free of any material.

FIGS. 11 to 13 illustrate further variants of passive sensors 1500, 1600, 1700, which can be used as alternatives to the passive sensor 1100 for the passive sensing means 101' of the embodiment illustrated in FIG. 9. The reader is therefore referred back to the description above regarding any features previously described of the passive sensors 1500, 1600, 1700.

In the embodiment illustrated in FIG. 11, like the passive sensor 1100 of the embodiment illustrated in FIG. 10, the passive sensor 1500 is a resonant circuit comprising an inductive element, here inductor 1501, having first spires 15011 on a first main side of a carrier substrate and at least one spire 15012 on a second side of the carrier substrate, opposite the first main side. However, in contrast with the passive sensor 1100 illustrated in FIG. 10, while the spires 15011 on the first main side have the same configuration as the spires 11011 of the inductor 1101, in the embodiment illustrated in FIG. 11, the outermost spire of the at least one spire 15012 on the second main side is on a larger circumference than any of the spires 15011 of the first main side. Thus, while FIG. 11 schematically illustrates only one spire 15012, it would be possible to have more than one spire 15012 on the second main side before the inductor 1501 continues on the first main side with the via 15053.

Other than the difference relating to the at least one spire 15012 on the second main side, the inductor 1501 of the embodiment illustrated in FIG. 11 is substantially of the same type as the inductor 1101 of the embodiment illustrated in FIG. 10. Thus, it can also comprise concave arc-shaped segments 15071, 15072, 15073 with respect to—but not centered on—a substantially central reference point 1510 of the passive sensor 1500, as well as convex arc-shaped segments 15021, 15022, 15023 joining the concave segments 15071, 15072, 15073 to one another. Similarly, the inductor 1501 can further comprise straight inductor segments 15031, 15032, 15033, 15034, 15035, 15036 and rounded junctions 15041, 15042, 15043, 15044, 15045, 15046 between the straight segments 15031, 15032, 15033, 15034, 15035, 15036 and the concave segments 15071, 15072, 15073.

Also like the inductor 1101 illustrated in FIG. 10, the inductor 1501 of the embodiment illustrated in FIG. 11 can also comprise a first terminal 15051 on the innermost spire of the plurality of spires 15011 on the first main side of the carrier substrate, and a second terminal 15052 on the outermost circumference of the at least one spire 15012 on the second main side of the carrier substrate, as well as small deflected areas 1506 between successive spires. The first main side of the inductor 1501 can also comprise for instance between about 5 to 20 spires 15011, preferably 8 to 15 spires 15011, more preferably 10 to 13 spires 15011, and its width can also preferably be kept below about 2.0 mm, for instance at about 1.5 mm or even below. Also similarly, the second main side can comprise up to 5 spires 15012. However, for the sake of simplicity, the inductor 1501 is illustrated in FIG. 11 with the same amount of spires 15011, 15012 on the first and second main sides as the inductor 1101 in FIG. 10.

In the embodiment illustrated in FIG. 11, the passive sensor 1500 further comprises at least one capacitive element, here the three capacitors 1521, 1522, 1523, which are all coplanar in one layer with the spires 15011 on the first main side of the carrier substrate, prior to any deformation of the passive sensor 1500 for its incorporation in a contact lens of a physiological parameter monitoring system. Thus, the capacitors 1521, 1522, 1523 are essentially the same as in the passive sensor 600 of the embodiment illustrated in FIG. 6. Thus, in contrast with the embodiment illustrated in FIG. 10, only one capacitor 1521, 1522, 1523 is provided at the inner circumference of each concave arc-shaped segment 15071, 15072, 15073, respectively, and while each capacitor 1521, 1522, 1523 is also coplanar, the first and second electrodes in each pair of electrodes 15211 and 15212, 15221 and 15222, 15231 and 15232, are not interdigitated with each other but is, itself, an interdigitated electrode. As further illustrated, each individual electrode 15211, 15212, 15221, 15222, 15231, 15232 of the passive sensor 1500 can cover roughly at least as much surface as a full interdigitated capacitor 1121, 1122, 1123, 1124, 1125, 1126 of the passive sensor 1100 of the embodiment referring to FIG. 10. In terms of shape, by analogy to the embodiments illustrated in FIGS. 5 and 6, compared to the embodiment illustrated in FIG. 10, in the embodiment illustrated in FIG. 11, each electrode 15211, 15212, 15221, 15222, 15231, 15232 roughly corresponds to having the two interdigitated E-shaped electrodes 11211 and 11212, 11221 and 11222, 11231 and 11232, 11241 and 11242, 11251 and 11252, and 11261 and 11262 of each capacitor 1121, 1122, 1123, 1124, 1125, 1126 joined at their largest extremity—towards the innermost spire of the inductor 1101—thereby forming a single integral interdigitated electrode. An advantage of shaping the individual electrodes 15211, 15212, 15221, 15222, 15231, 15232 in this way is that it facilitates the molding or shaping of the passive sensor 1500 for its attachment to a contact lens. As illustrated in FIG. 11, in an analog manner to the embodiment illustrated in FIG. 10, the back of the electrodes 15211, 15212, 15221, 15222, 15231, 15232 facing the convex arc-shaped segments 15021, 15022, 15023 of the inductor 1501 can also follow the arc-shaped geometry of the convex arc-shaped segments 15021, 15022, 15023 and broaden towards the central area 1530, with the same advantage over the prior art of improving the coverage of the underlying surface of the eye, in particular over the cornea, once the passive sensor 1500 is attached to the physiological parameter monitoring device 100, 100'.

Furthermore, like in the embodiment illustrated in FIG. 10, the first electrodes 15211, 15221, 15231 of the passive sensor 1500 can be provided as integral extensions of the innermost of the spires 15011 on the first main side of the carrier substrate, while the second electrodes 15212, 15222, 15232 can be connected to the spire 15012 of the second main side by means of respective electrically conductive vias 15213, 15223, 15233, which can also comprise a respective bridge with the spire 15012. FIG. 11 also illustrates that the vias 15213, 15223, 15233 can cross the substrate and even the second electrodes 15212, 15222, 15232. An advantage of this configuration in the embodiment illustrated in FIG. 11 is, in comparison to the embodiment illustrated in FIG. 10, that the number of electrically connecting vias is halved, thereby reducing the amount of areas where material crosses the carrier substrate, while keeping at least the same amount of surface covered by coplanar capacitors.

In the embodiment illustrated in FIG. 12, like the passive sensors 1100, 1500 of the embodiments illustrated in FIGS. 10 and 11, the passive sensor 1600 is also a resonant circuit comprising an inductive element, here inductor 1601, with more spires 16011 on the first main side of a carrier substrate than spires 16012 on the second main side thereof. The passive sensor 1600 also comprises at least one capacitive element, here the plurality of coplanar capacitors 1621, 1622, 1623, 1624, 1625, 1626, 1627, 1628, which are in particular also coplanar in one layer with the spires 16011 on the first main side prior to any deformation of the passive sensor 1600 for its attachment to the inner surface 103 of the first contact lens element 102 in the physiological parameter monitoring system 100, 100'. Again, for clarity purposes, the carrier substrate and any optional protective coating layers thereon are not illustrated.

Following a preferred variant, analogously to the embodiments illustrated in FIGS. 7 and 8, and in alternative to the embodiments illustrated in FIGS. 10 and 11, the inductor 1601 of the embodiment illustrated in FIG. 12 is a circular ring-shaped inductor spiraling from a first terminal 16051 on the innermost spire of the plurality of spires 16011 on the first main side towards a second terminal 16052 on the outermost circumference of the at least one spire 16012 on the second main side, and the connection between the spires 16011, 16012 can be provided through the carrier substrate by means of a conductive via 16053. While the inductors 1101 and 1501 of the previous embodiments and their variants can be more advantageous in terms of facilitating the deformation of the passive sensors 1100, 1500 in view of their attachment to the concave cap-shaped inner surface 103 of the first contact lens element 102, the ring-shaped inductor 1601 of the passive sensor 1600 of the embodiment illustrated in FIG. 12 is in turn more advantageous in terms of the amplitude of the signal at the antenna of a complementary portable device generating the external magnetic field. Like in the previous embodiments, the inductor 1601 can also comprise for instance about 5 to 20 spires 16011 on the first main side, preferably 8 to 15 spires 16011, more preferably 10 to 13 spires 16011, and up to 5 spires 16012 on the second main side. Its width can also preferably be kept below about 2.0 mm, for instance at about 1.5 mm or even below. Like the inductors 1101, 1501 of the embodiments illustrated in FIGS. 10 and 11, the inductor 1601 of the embodiment illustrated in FIG. 12 is shown with 12 spires 16011 on the first main side, which can have a width of about 50 μm and be spaced apart by also about 50 μm, and one spire 16012 on the second main side. However, also like in the previous embodiments, the width of the spires 16011, 16012 and/or the distance between successive spires 16011 or 16012 could be chosen in a range from about 30 μm to about 100 μm, preferably between about 40 μm and about 80 μm and don't need to be the same.

In order to provide sufficient surface coverage in view of using the passive sensor 1600 for detecting deformations of the surface of an eye while still providing for sufficient flexibility for an attachment to a contact lens, in the embodiment illustrated in FIG. 12, a plurality of capacitors are provided, here the eight coplanar interdigitated capacitors 1621, 1622, 1623, 1624, 1625, 1626, 1627, 1628. In view of the description above, the skilled person will understand that this number should not be seen as restrictive, and that more or less capacitors can be used depending on the desired configuration and sensitivity of the passive sensing means, as well as on the underlying surface coverage.

As further illustrated in FIG. 12, the capacitors 1621, 1622, 1623, 1624, 1625, 1626, 1627, 1628 are very similar to the capacitors of the embodiments illustrated in FIGS. 10 and 11 and are in particular like the capacitors of the embodiment illustrated in FIG. 7. Thus, the pairs of electrodes 16211 and 16212, 16221 and 16222, 16231 and 16232, 16241 and 16242, 16251 and 16252, 16261 and 16262, 16271 and 16272, and 16281 and 16282 are also coplanar to one another, forming interdigitated E-shapes. Furthermore, the capacitors 1621, 1622, 1623, 1624, 1625, 1626, 1627, 1628 can also be larger outwards from the central area 1630 than towards the central area 1630 but, in contrast to FIGS. 10 and 11, do not broaden again towards the central area 1630, such that the overall shape of each capacitor 1621, 1622, 1623, 1624, 1625, 1626, 1627, 1628 is essentially trapezoidal but also arched following the shape of the inductor 1101, with the larger base facing outwards from the central area 1630 and the smaller base facing towards said central area 1630, with the same advantages as described for the previous embodiments.

Furthermore, as described also for the embodiments illustrated in FIGS. 10 and 11, in the passive sensor 1600 of the embodiment illustrated in FIG. 12, the first electrodes 16211, 16221, 16231, 16241, 16251, 16261, 16271, 16281 can also be electrically connected to and be provided as integral extensions of the innermost spire of the plurality of spires 16011 on the first main side of the inductor 1601, while the second electrodes 16212, 16222, 16232, 16242, 16252, 16262, 16272, 16282 can be connected to the spire 16012 on the second main side by means of respective electrically conductive vias 16213, 16223, 16233, 16243, 16253, 16263, 16273, 16283 as also described above for the previous embodiments.

In the embodiment illustrated in FIG. 13, the passive sensor 1700 is also a resonant circuit comprising an inductive element, here the same inductor 1601 as in the embodiment illustrated in FIG. 12, and at least one capacitive element, here the four capacitors 1721, 1722, 1723, 1724, which are all coplanar in one layer prior to any deformation of the passive sensor 1700 for its attachment to the first contact lens element 102. The reader is referred to the description above in particular regarding specifically the inductor 1601, as well as other features in common with the passive sensors 1100, 1500, 1600 or with the passive sensors 200, 500, 600, 700, 800 of the previous embodiments.

In contrast with the embodiment illustrated in FIG. 12, but similarly to the embodiments illustrated in FIGS. 8 and 11, in the passive sensor 1700, the first and second electrodes in each pair of electrodes 17211 and 17212, 17221 and 17222, 17231 and 17232, 17241 and 17242 of the capacitors 1721, 1722, 1723, 1724 are not interdigitated with each other. However, as illustrated in FIG. 13, each individual electrode 17211, 17212, 17221, 17222, 17231, 17232, 17241, 17242 can be in the shape of a trident pointing towards the central area 1630, forming also an overall trapezoidal shape as described above, wherein the capacitors 1721, 1722, 1723, 1724 are also larger towards the outside than towards the central area 1630 and their larger base can follow the rounded geometry of the inductor 1601, with again the same advantages as described above for instance for the embodiment illustrated in FIG. 10. As further illustrated in FIG. 13, each individual electrode 17211, 17212, 17221, 17222, 17231, 17232, 17241, 17242 of the passive sensor 1700 can cover roughly at least as much surface as a full interdigitated capacitor 1621, 1622, 1623, 1624, 1625, 1626, 1627, 1628 of the embodiment illustrated in FIG. 12.

Furthermore, like in the previous embodiments, the first electrodes 17211, 17221, 17231, 17241 of the passive sensor 1700 can be electrically connected to the innermost spire of the plurality of spires 16011 on the first main side of the inductor 1601 and can be provided as integral extensions thereof, while the second electrodes 17212, 17222, 17232, 17242 can be connected to the spire 16012 on the second main side by means of respective electrically conductive vias 17213, 17223, 17233, 17243 and respectively associated conductive bridges. Like in the embodiment illustrated in FIG. 11, an advantage of this configuration in the embodiment illustrated in FIG. 13 is, in comparison to the embodiment illustrated in FIG. 12, that the number of electrically connecting vias is halved, thereby reducing the amount of areas where material crosses the carrier substrate, while keeping at least the same amount of surface covered by coplanar capacitors.

As mentioned above, any of the passive sensors 200, 500, 600, 700, 800 of the embodiments illustrated in FIG. 4 to 8, or any variant thereof, can be used in the physiological parameter monitoring devices 100, 100' of the embodiments illustrated in FIGS. 1 and 2, preferably in the variant illustrated in FIG. 3. Similarly, any of the passive sensors 1100, 1500, 1600, 1700 of the embodiments illustrated in FIG. 10 to 13, or any variants thereof, can be used in the physiological parameter monitoring devices 100, 100', preferably in the variant illustrated in FIG. 9. Indeed, when the passive sensing means 200, 500, 600, 700, 800 or 1100, 1500, 1600, 1700 respond to an external magnetic field generated by a complementary portable device, the configuration of the inductor and/or of the coplanar capacitors allows the electric field lines generated therein to protrude out of the plane of the respective passive sensors 200, 500, 600, 700, 800 or 1100, 1500, 1600, 1700. Thus, when used in any of the physiological parameter monitoring devices 100, 100' and their variants, parasitic capacitances will exist with the underlying eye tissue and/or tear film thereon, which will form sensing capacitors, wherein the spires of the inductor and/or the physical capacitors of the passive sensors 200, 500, 600, 700, 800 or 1100, 1500, 1600, 1700 are first electrodes of said sensing capacitors, and the eye tissue and/or the tear film are the second electrodes thereof.

The skilled person will find it obvious that the embodiments described above can be combined in order to provide further embodiments of the various aspects of the present invention. In particular, the variants of a passive sensor can all be used in any of the variants of the physiological parameter monitoring device.

The skilled person will also appreciate that the present invention provides an improvement in the field of passive sensing devices for monitoring variations of a physiological parameter, in particular for monitoring variations of the intraocular pressure. The physiological parameter monitoring device according to preferred variants of the present invention can be used advantageously for patients suffering from glaucoma and related eye diseases. Compared to solutions known in the art, the aspects of the present invention provide a multilayered contact lens including a passive sensing device with improved sensitivity to deformations of the surface of the eye. In particular, the aspects of the present invention provide a physiological parameter monitoring device having a multilayered contact lens structure that can have a rigid and a soft contact lens enclosing a variable space, and wherein the passive sensing means only needs to be attached to the first contact lens element, thereby providing a simplified and improved physiological parameter monitoring device.

The invention claimed is:

1. A physiological parameter monitoring device, for detecting variations of intraocular pressure in a patient's eye, comprising:
   a first contact lens element having an inner surface and an outer surface opposite the inner surface, wherein at least the outer surface of the first contact lens element is adapted for contacting an ocular tissue comprising eyelid tissue; and
   a second contact lens element having an inner surface and an outer surface opposite the inner surface, wherein at least the inner surface of the second contact lens element is adapted for contacting an ocular tissue comprising at least the cornea and/or a tear film thereon;
   wherein the first contact lens element and the second contact lens element are attached to one another at a peripheral attachment area, thereby enclosing an intermediate space; and
   further comprising a passive sensing means forming a resonant circuit for detecting variations of the physiological parameter;
   characterized in that the passive sensing means is provided only in or on the first contact lens element, and wherein said intermediate space is filled with a dielectric material having a relative permittivity value $\varepsilon_r$, of less than the relative permittivity of a tear film and/or an ocular tissue at ambient temperature.

2. The physiological parameter monitoring device of claim 1, wherein the passive sensing means is provided towards the inner surface of the first contact lens element.

3. The physiological parameter monitoring device of claim 1, wherein the inner surface of the first contact lens element comprises a recess for accommodating the passive sensing means.

4. The physiological parameter monitoring device parameter monitoring device of claim 1, wherein the relative permittivity value, $\varepsilon_r$, is less than 10 times the relative permittivity of a tear film and/or ocular tissue at ambient temperature.

5. The physiological parameter monitoring device parameter monitoring device claim 1, wherein a distance (d) between the passive sensing means and the inner surface of the second contact lens element is smaller than a distance (D) between the passive sensing means and the outer surface of the first contact lens element.

6. The physiological parameter monitoring device parameter monitoring device of claim 1, wherein the second contact lens element comprises a flexible material.

7. The physiological parameter monitoring device of claim 6, wherein the second contact lens element is a soft contact lens configured to extend at least over the cornea.

8. The physiological parameter monitoring device of claim 1, wherein the patient's eye comprises a cornea, a sclera and a limbus and wherein the second contact lens element is configured to extend over the cornea and part of the sclera, leaving a non-contact area at the limbus.

9. The physiological parameter monitoring device of claim 1, wherein the first contact lens element comprises a rigid polymer material.

10. The physiological parameter monitoring device of claim 9, wherein the first contact lens element is a rigid scleral contact lens.

11. The physiological parameter monitoring device according to claim 1, wherein the patient's eye comprises a sclera and wherein the peripheral attachment area is an area configured to contact the sclera.

12. The physiological parameter monitoring device of claim 1, wherein the passive sensing means is a resonant circuit comprising an inductor and at least one coplanar capacitor.

13. The physiological parameter monitoring device of claim 12, wherein the inductor is a spiral inductor comprising a plurality of spires on a first main side of a carrier substrate, which are coplanar with said at least one coplanar capacitor.

14. The physiological parameter monitoring device of claim 13, wherein the inductor further comprises at least one spire on a second main side of the carrier substrate, opposite the first main side.

15. The physiological parameter monitoring device of claim 12, wherein the at least one capacitor comprises a first electrode and a second electrode, and wherein the at least one capacitor and the first electrode and the second electrode are interdigitated.

16. The physiological parameter monitoring device of claim 1, wherein the passive sensing means is provided over the inner surface of the first contact lens element.

17. The physiological parameter monitoring device of claim 1, wherein the dielectric material comprises a compressible dielectric material.

18. The physiological parameter monitoring device of claim 6, wherein the flexible material comprises a flexible polymer material.

19. The physiological parameter monitoring device of claim 6, wherein the flexible material comprises a hydrophilic flexible polymer material.

20. The physiological parameter monitoring device of claim 4, wherein the relative permittivity value, $\varepsilon_r$, is between 1 and 5.

* * * * *